(12) United States Patent
Pipes et al.

(10) Patent No.: US 12,102,696 B2
(45) Date of Patent: Oct. 1, 2024

(54) RADIOLABELING AND FORMULATION FOR SCALE UP OF $^{64}$Cu-DOTATATE

(71) Applicant: Curium US LLC, St. Louis, MO (US)

(72) Inventors: David Pipes, St. Louis, MO (US); Lauren Radford, St. Louis, MO (US); Shaun Loveless, St. Louis, MO (US); Allan Casciola, St. Louis, MO (US)

(73) Assignee: Curium US, LLC, St. Louis, MO (US)

( * ) Notice: Subject to any disclaimer, the term of this patent is extended or adjusted under 35 U.S.C. 154(b) by 0 days.

(21) Appl. No.: 17/467,110

(22) Filed: Sep. 3, 2021

(65) Prior Publication Data

US 2022/0080059 A1     Mar. 17, 2022

Related U.S. Application Data

(60) Provisional application No. 63/074,451, filed on Sep. 3, 2020.

(51) Int. Cl.
*A61K 51/04*     (2006.01)
*A61K 51/08*     (2006.01)

(52) U.S. Cl.
CPC ........ *A61K 51/0472* (2013.01); *A61K 51/083* (2013.01)

(58) Field of Classification Search
None
See application file for complete search history.

(56) References Cited

U.S. PATENT DOCUMENTS

| | | | |
|---|---|---|---|
| 4,298,591 A | 11/1981 | O'Brien, Jr. et al. | |
| 9,061,078 B2 | 6/2015 | Yoo et al. | |
| 2010/0256331 A1 | 10/2010 | Velikyan et al. | |
| 2012/0178920 A1 | 7/2012 | Kim et al. | |
| 2014/0341807 A1 | 11/2014 | Kjaer et al. | |
| 2020/0131224 A1 | 4/2020 | Fugazza et al. | |

FOREIGN PATENT DOCUMENTS

| | | |
|---|---|---|
| CA | 2478137 A1 | 2/2006 |
| CA | 2345838 C | 2/2010 |
| CN | 103645254 B | 1/2015 |
| RU | 2223118 C1 | 2/2004 |
| RU | 2614235 C2 | 3/2017 |
| WO | 2019/020831 A1 | 1/2019 |

OTHER PUBLICATIONS

Aguilar-Ortiz, E., et al., "Synthesis, characterization and evaluation of a Cu-labeled macrocyclic-porphyrin as a potential chelator for Cu-based radiopharmaceuticals," Journal of Radioanalytical and Nuclear Chemistry, Apr. 2019, vol. 320, Issue 1, pp. 79-86 (Abstract).
Prakash, G. K. S., et al., "Expedient synthesis of [18 F]-labeled alfa-trifluoromethyl ketones," J Label Compd Radiopharm, 2003, 46, pp. 1087-1092.
Monier, M., et al., "Adsorption of Cu (II), Co (II), and Ni (II) ions by modified magnetic chitosan chelating resin," Journal of Hazardous Materials, 2010, 177, pp. 962-970.
Seo, J. W., et al., "A novel method to label preformed liposomes with 64Cu for positron emission tomography (PET) imaging," Bioconjug Chem., 2008, 19(12) pp. 2577-2584 (Author Manuscript; 19 pages).
Cleeren, F., et al., "New Chelators for Low Temperature Al18 F-Labeling of Biomolecules," Bioconjugate Chem., 2016, 27, pp. 790-798.
Baraka, A., et al., "Preparation and characterization of melamine-formaldehyde-DTPA chelating resin and its use as an adsorbent for heavy metals removal from wastewater," Reactive & Functional Polymers, 2007, 67, pp. 585-600.
International Search Report, Written Opinion and Search History received in PCT/US21/49167 and mailed on Feb. 15, 2022.
Andersen, T.L., et al., "Improving contrast and detectability: Imaging with [55Co]Co-DOTATATE in comparison with [64Cu]Cu-DOTATATE and [68Ga]Ga-DOTATATE," Journal of Nuclear Medicine, 61(2), pp. 228-233 (2020).
Yuan, J., et al., "Synthesis of poly [APMA]-DOTA-64Cu conjugates for interventional radionuclide therapy of prostate cancer: assessment of intratumoral retention by micro-positron emission tomography," Molecular Imaging, 6(1), pp. 10-17 (2007).

*Primary Examiner* — Jennifer Chin
(74) *Attorney, Agent, or Firm* — Mayer Brown LLP

(57) ABSTRACT

The present disclosure relates to methods to create a robust procedure capable of supplying commercial quantities of a radioactive diagnostic agent indicated for use with positron emission tomography (PET) for localization of somatostatin receptor positive neuroendocrine tumors (NETs) in adult patients.

7 Claims, 5 Drawing Sheets

RADIOLABELING AND FORMULATION FOR SCALE UP OF $^{64}$Cu-DOTATATE

RELATED CASE

This application claims priority to U.S. Provisional Application No. 63/074,451 filed on Sep. 3, 2020, which is incorporated herein by reference in its entirety to the full extent permitted by law.

TECHNICAL FIELD

The present disclosure relates to the compositions and methods for radiolabeling and purification of $^{64}$Cu-DOTATATE, a bioconjugate compound containing a positron-emitting radionuclide.

BACKGROUND

Known imaging techniques with tremendous importance in medical diagnostics are positron emission tomography (PET), computed tomography (CT), magnetic resonance imaging (MRI), single photon computed tomography (SPECT) and ultrasound (US). Although today's imaging technologies are well developed, they rely mostly on non-specific, macroscopic, physical, physiological, or metabolic changes that differentiate pathological from normal tissue.

Targeting molecular imaging (MI) has the potential to reach a new dimension in medical diagnostics. The term "targeting" is related to the selective and highly specific binding of a natural or synthetic ligand (binder) to a molecule of interest (molecular target) in vitro or in vivo.

MI is a rapidly emerging biomedical research discipline that may be defined as the visual representation, characterization and quantification of biological processes at the cellular and sub-cellular levels within intact living organisms. It is a novel multidisciplinary field, in which the images produced reflect cellular and molecular pathways and in vivo mechanism of disease present within the context of physiologically authentic environments rather than identify molecular events responsible for disease.

Several different contrast-enhancing agents are known today. They can be used in functional imaging are mainly developed for PET and SPECT. The application of radiolabeled bioactive peptides for diagnostic imaging is gaining importance in nuclear medicine. Biologically active molecules which selectively interact with specific cell types are useful for the delivery of radioactivity to target tissues. For example, radiolabeled peptides have significant potential for the delivery of radio nuclides to tumors, infarcts, and infected tissues for diagnostic imaging and radiotherapy.

DOTA (1,4,7,10-tetrakis(carboxymethyl)-1,4,7,10 tetraazacyclo dodecane) and its derivatives constitute an important class of chelators for biomedical applications as they accommodate very stably a variety of di- and trivalent metal ions. One of its derivatives is DOTATATE, [(4,7,10-Tricarboxymethyl-1,4,7,10-tetrazacyclododec-1-yl)acetyl]-(D)-Phenylalanyl-(L)-Cysteinyl-(L)-Tyrosyl-(D)-Tryptophanyl-(L)-Lysyl-(L)-Threoninyl-(L)-Cysteinyl-(L)-Threonine-cyclic(2-7)disulfide which can be used as a targeting agent. The chemical structure of DOTATATE is shown below.

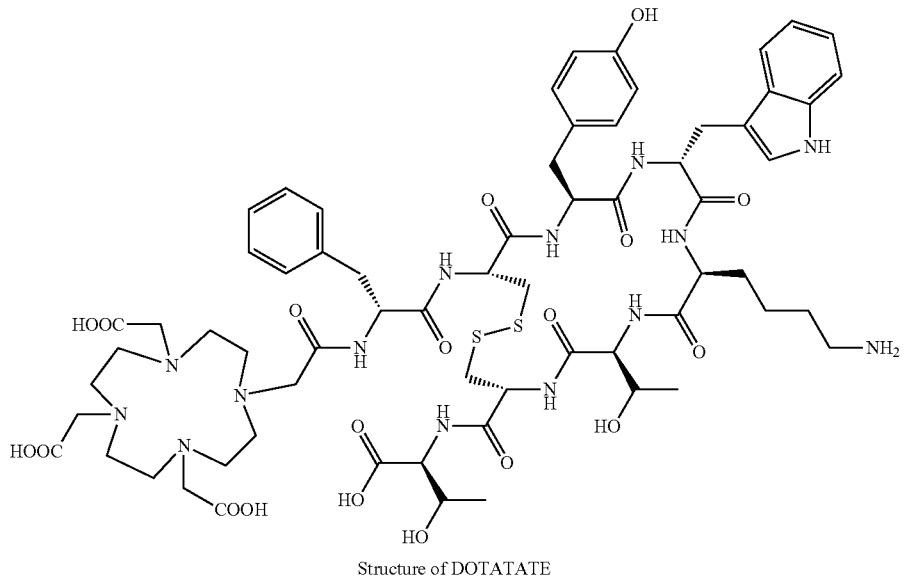 [SMILES: CC(O)[C@H](NC(=O)[C@@H]1CSSC[C@H](NC(=O)[C@@H](Cc2ccccc2)NC(=O)CN2CCN(CC(=O)O)CCN(CC(=O)O)CCN(CC(=O)O)CC2)C(=O)N[C@@H](Cc2ccc(O)cc2)C(=O)N[C@H](Cc2c[nH]c3ccccc23)C(=O)N[C@@H](CCCCN)C(=O)N[C@@H](C(C)O)C(=O)N1)C(=O)O]

Structure of DOTATATE

An emerging area is the use of chelator conjugated bioactive peptides for labeling with radiometals in different fields of diagnostic and therapeutic nuclear oncology. There have been several reports in recent years on targeted radiotherapy with radiolabeled somatostatin analogs. $^{68}$Ga-DOTATATE (Dedden S. A., et al.; J Nucl Med; 2016 vol. 57 no. 6 872-878), $^{68}$Ga-DOTATOC (Nicolas, G. P., et al.; J Nucl Med; 2018 vol. 59 no. 6 915-921), $^{68}$Ga-DOTANOC (Amdrosini V., et al.; J Nucl Med; 2010 vol. 51 no. 5 669-673) are known PET tracers used for visualizing NETs and $^{177}$Lu-DOTATATE is used for radionuclide therapy (Strosberg, J. et al.; N Engl J Med 2017; 376:125-135). However, there exists a need for further peptide-based compounds having utility for diagnostic imaging techniques, such as PET.

Copper-64 ($^{64}$Cu) is a positron-emitting radionuclide that is well-suited for use as a diagnostic agent for positron emission tomography (PET). Its 12.7 h half-life is long enough to allow for post-production processing, labeling and shipping and its average positron energy of 0.28 MeV provides high-resolution images. Importantly, the large cross-section of the $^{64}$Ni (p,n)$^{64}$Cu reaction allows for production of commercial quantities. The PET radioisotope, copper-64 (Cu-64), has been radiolabeled to the chelate-peptide conjugate, DOTATATE, for diagnostic imaging of neuroendocrine tumors in humans.

The complete chemical structure for the Cu-DOTATATE complex has not been determined with an X-ray crystal structure analysis, however the Cu-DOTA complex has been structurally determined by X-ray crystal analysis. In crystalline form, the Cu-DOTA complex has been shown to be 6-coordinate utilizing the 4 amino nitrogen atoms and 2 carboxylate oxygen atoms as set forth below.

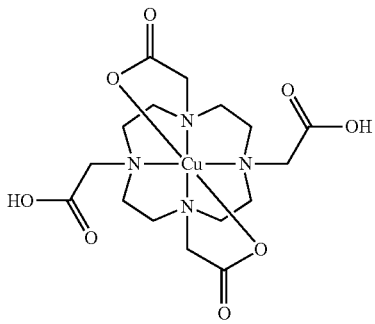

Structural Drawing of one isomer of Cu-DOTA

Two of the carboxylic acid groups are left free and uncoordinated to the copper metal ion. Therefore, the attachment of the peptide through one of the carboxylic acids to form the linking amide bond is not expected to change the coordination of copper to the DOTATATE peptide.

$^{64}$Cu-DOTATATE binds to somatostatin receptors with highest affinity for subtype 2 receptors (SSTR2). It binds to cells that express somatostatin receptors including malignant neuroendocrine cells, which overexpress SSTR2 receptors. $^{64}$Cu is a positron ($\beta^+$) emitting radionuclide with an emission yield that allows positron emission tomography (PET) imaging. When the imaging capabilities of $^{64}$Cu are combined with the receptor-targeting abilities of DOTATATE, the result is $^{64}$Cu-DOTATATE, a radiopharmaceutical agent, that is capable of imaging somatostatin-receptor-expressing neuroendocrine tumors (NETs).

Nowadays, $^{64}$Cu-DOTATATE is prepared for use at the site of preparation in low total radioactivity for a very limited number of patients. As such, there remains an unmet need to provide an improved process for making high-purity $^{64}$Cu-DOTATATE and scale up the radiolabeling production of $^{64}$Cu-DOTATATE while maintaining stability sufficient to transport the drug product to patients in the hospital.

SUMMARY

The present disclosure satisfies the above needs and relates to methods to provide a useful process capable of supplying commercial quantities of the copper labeled drug product, $^{64}$Cu-DOTATATE.

The purpose of this invention is to show and confirm the discovery that labeling copper at lower temperatures (≤30° C.) has the advantage of improving the purity of the drug product as many other common metal impurities actual labeling significantly slower than copper to the chelate such as DOTATATE. Previous studies on the radiolabeling of copper radioisotopes (i.e. $^{64}$Cu, $^{67}$Cu) have typically been done at elevated temperatures such as 40° C. to 95° C. The elevated temperature was used to speed up the labeling process and to ensure maximum radiolabeling of the copper to the chelate. Some literature reviews have shown labeling at room temperature can achieve sufficient labeling. The present disclosure teaches that one can use the more rapid labeling kinetics of copper compared to the slower labeling kinetics of the other metals to obtain a purer product.

Provided herein are the following: $^{64}$Cu-DOTATATE preparation, Design of Experiment (DOE) to monitor final formulation parameters and their effect on $^{64}$Cu-DOTATATE stability, scale up experiments for preparing 500 mCi-2000 mCi of $^{64}$Cu-DOTATATE, stability of $^{64}$Cu-DOTATATE in its final formulation, optimization of the quantity of DOTATATE used relative to the total activity used for radiolabeling, and the effect of the specific activity of $^{64}$Cu copper chloride solution on $^{64}$Cu-DOTATATE purity.

For example, provided herein are methods for radiolabeling DOTATATE comprising the steps of reacting Copper-64 with a buffered solution comprising DOTATATE, where the reaction occurs in less than 15 minutes at a temperature of less than or equal to 30° C. and the mole ratio of DOTATATE to Copper-64 in the reaction solution is from about 110:1 to about 90:1.

Further provided herein are methods for preparing drug products comprising $^{64}$Cu-DOTATATE, where the drug product is prepared by (i) radiolabeling DOTATATE with Copper-64 at a concentration of about 0.6 μg/mL (μg of DOTATATE per mCi of Copper-64) and the radionuclidic purity of Copper-64 in the drug product is about 99%.

Also provided herein are drug products for use in positron emission tomography comprising $^{64}$Cu-DOTATATE, wherein the $^{64}$Cu-DOTATATE is stored in a single-dose vial containing 148 MBq of $^{64}$Cu-DOTATATE, wherein the radioactive concentration of the drug product is about 5-15 mCi/mL and wherein the radiochemical purity of the drug product after dilution is ≥96%.

BRIEF DESCRIPTION OF THE DRAWINGS

The foregoing features of embodiments will be more readily understood by reference to the following detailed description, taken with reference to the accompanying drawings, in which.

DETAILED DESCRIPTION

Figure 1A:
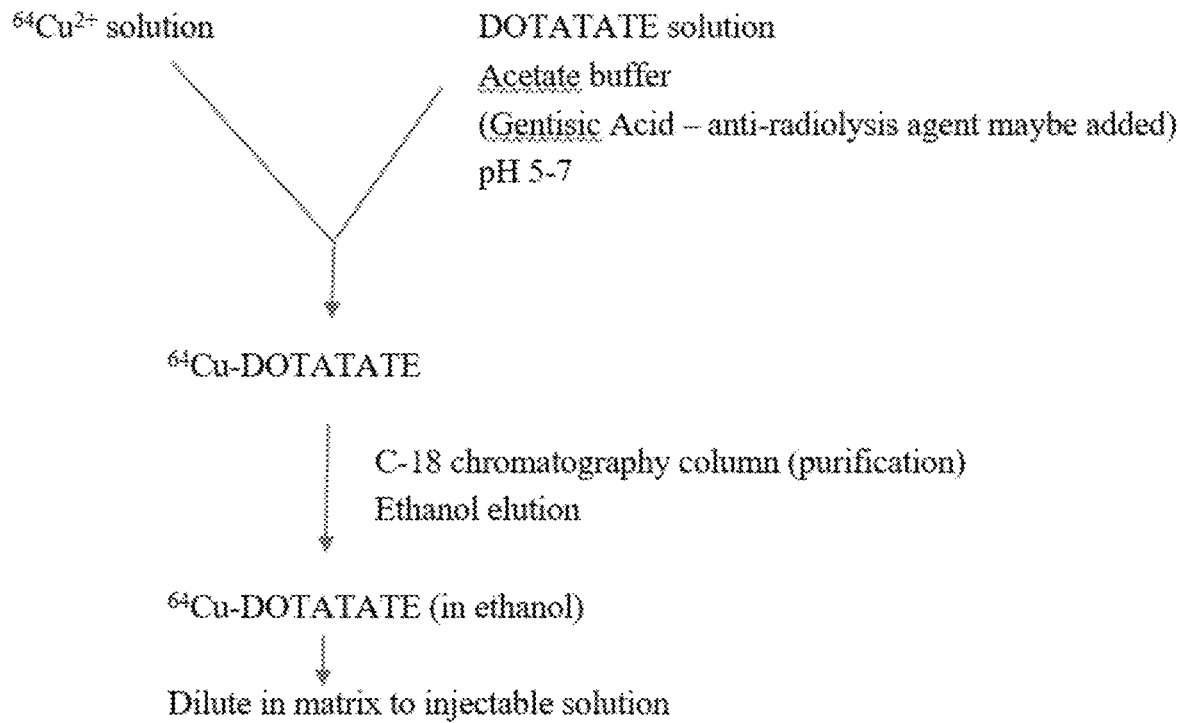
FIG. 1(A) presents a general radiolabeling and formulation scheme.

The various aspects and embodiments will now be fully described herein. These aspects and embodiments may, however, be embodied in many different forms and should not be construed as limiting; rather, these embodiments are provided so the disclosure will be thorough and complete, and will fully convey the scope of the present subject matter to those skilled in the art. All publications, patents and patent applications cited herein, whether supra or infra, are hereby incorporated by reference in their entirety.

A. Definitions

Unless defined otherwise, all terms and phrases used herein include the meanings that the terms and phrases have attained in the art, unless the contrary is clearly indicated or clearly apparent from the context in which the term or phrase is used. Although any methods and materials similar or equivalent to those described herein can be used in the practice or testing of the present invention, particular methods and materials are now described.

Unless otherwise stated, the use of individual numerical values are stated as approximations as though the values were preceded by the word "about" or "approximately." Similarly, the numerical values in the various ranges specified in this application, unless expressly indicated otherwise, are stated as approximations as though the minimum and maximum values within the stated ranges were both preceded by the word "about" or "approximately." In this manner, variations above and below the stated ranges can be used to achieve substantially the same results as values within the ranges. As used herein, the terms "about" and "approximately" when referring to a numerical value shall have their plain and ordinary meanings to a person of ordinary skill in the art to which the disclosed subject matter is most closely related or the art relevant to the range or element at issue. The amount of broadening from the strict numerical boundary depends upon many factors. For example, some of the factors which may be considered include the criticality of the element and/or the effect a given amount of variation will have on the performance of the claimed subject matter, as well as other considerations known to those of skill in the art. As used herein, the use of differing amounts of significant digits for different numerical values is not meant to limit how the use of the words "about" or "approximately" will serve to broaden a particular numerical value or range. Thus, as a general matter, "about" or "approximately" broaden the numerical value. Also, the disclosure of ranges is intended as a continuous range including every value between the minimum and maximum values plus the broadening of the range afforded by the use of the term "about" or "approximately." Consequently, recitation of ranges of values herein are merely intended to serve as a shorthand method of referring individually to each separate value falling within the range, and each separate value is incorporated into the specification as if it were individually recited herein.

The terms "drug product" or "$^{64}$Cu-DOTATATE Injection" are used interchangeably herein and refers to the $^{64}$Cu-DOTATATE in its final formulation used as a radioactive diagnostic agent.

"Optional" or "optionally" means that the subsequently described element, component or circumstance may or may not occur, so that the description includes instances where the element, component, or circumstance occurs and instances where it does not.

The terms "subject" or "patient" are used interchangeably herein and refers to a human or other mammal.

B. Introduction

The present disclosure relates to improved radiolabeling and formulation for scale up of $^{64}$Cu-DOTATATE preparation; FIG. 1(A).

The high-resolution imaging modality of positron emission tomography (PET) can be used in oncology to help clinicians gain a better understanding of a patient's disease status and monitor treatment efficacy allowing them to provide more effective and personalized care. One such PET agent is $^{64}$Cu-DOTATATE which targets and images neuroendocrine tumors (NETs) that overexpress somatostatin receptor subtype 2 (SSTR2), which can help identify patients who may benefit from receptor-targeted treatments. The imaging capability is afforded by $^{64}$Cu which is a positron-emitting radionuclide ($t_{1/2}$=12.7 h, $\beta^{+}_{avg}$=0.28 MeV, I=17.6% [represents intensity (I), which is sometimes reported as branching ratio (BR)] that can be imaged using PET while the targeting portion of the molecule is a modified version of octreotate (DOTA-D-Phe-Cys-Tyr-D-Trp-Lys-Thr-Cys-Thr, disulfide cyclized Cys2-Cys7), a cyclic peptide that mimics the native SSTR2-ligand somatostatin. These two functionalities are joined together by DOTA, a bifunctional chelator that remains bound to the N-terminal end of the peptide (forming DOTATATE) while simultaneously trapping $^{64}$Cu. The structure of $^{64}$Cu-DOTATATE (copper Cu 64 DOTATATE) is set forth below.

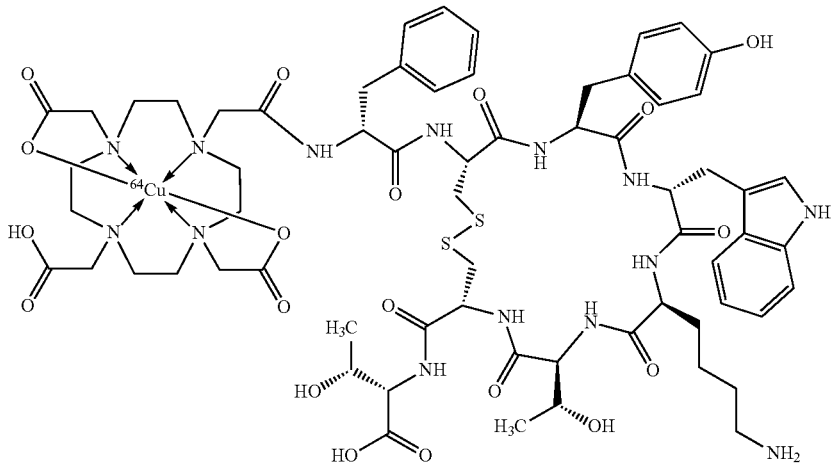

Structure of $^{64}$Cu-DOTATATE (copper Cu 64 DOTATATE)

The radiolabeling of DOTATATE with the radioisotope $^{64}$Cu was performed initially several decades ago. In past studies, small batches of $^{64}$Cu-DOTATATE were prepared for use at only the site of preparation in low total radioactivity for a very limited use and number of patients. Recently the radiolabeling was improved with higher radioactivity for the scale up into a commercial product. The final purified product was made at much higher initial total radioactivity levels and radiolysis was prevented with improved formulation and purification methods.

Scale up radiolabeling and formulation of large batches of drug were needed to be able to distribute the drug around the country. Scale up posed new problems and issues and new discoveries and solutions to achieve large batches of the drug. The current disclosure (i) explains improvements and changes to past studies and results and (ii) teaches conducted studies and scale up to large high activity batches.

Figure 1B:
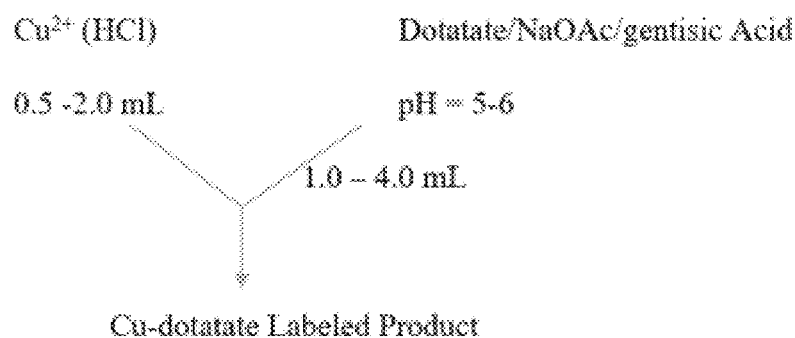
FIG. 1(B) presents a general radiolabeling and formulation scheme for the present invention.

The general radiolabeling and formulation scheme that has been used is shown in FIG. 1(B).

Specifically, the present disclosure teaches a significant scale up in the total radioactivity of $^{64}$Cu that can be radiolabeled and purified for the $^{64}$Cu-DOTATATE injection drug product.

Previous studies have been low to medium levels of radioactivity (mCi) of $^{64}$Cu. The current disclosure scaled up the total radioactivity to >5,400 mCi at radiolabeling. The challenges are in achieving radiolabeling without degradation due to radiolysis and due to competition of the DOTATATE with other metals than $^{64}$Cu. The radiolabeled product then must be purified quickly and diluted into a stabilizing solution immediately to prevent degradation from radiolysis so that the needed high radiochemical purity (RCP) is maintained.

The stability of the purified $^{64}$Cu-DOTATATE in its final formulation (5% ethanol in 45 mg/mL sodium ascorbate) was evaluated up to 48 h post-labeling and shows no significant degradation or loss of $^{64}$Cu from the complex.

To prepare $^{64}$Cu-DOTATATE, $^{64}$CuCl$_2$ in dilute HCl is reacted with DOTATATE in a sodium acetate buffer containing gentisic acid with a ratio of 2 μg DOTATATE/mCi. The reaction mixture is incubated and then purified into a sodium ascorbate (NaOAsc) buffer. The resulting $^{64}$Cu-DOTATE solution is sterile filtered and served as the final formulation. Development efforts disclosed herein focus on improving the production design space and scaling up the radiolabeling reaction to prepare ≥2 Ci of $^{64}$Cu-DOTATATE. Radiolabeling proven even at 15° C. in 5 minutes. Purified product was accomplished at up to 10,000 mCi $^{64}$Cu-DOTATATE. Purified product was achieved with 50% ethanol in water (previous literature indicated just pure ethanol). Indeed, the use of 50% ethanol in water improved the purified product yield as compared to the use of 100% ethanol.

Purified drug product (2 mL) was diluted immediately into large volumes (>20 mL; but normally for 2000-10,000 mCi product in >100 mL) which prevented degradation (radiolysis) and maintained required RCP of >95%. Previous literature diluted purified product into <20 mL.

Final Drug Product was stabilized for up to 48 hours post purification using 28 to 122 mg/mL sodium ascorbate with 1-5% ethanol with RCP>95%. Previous RCP stabilization for 48 hours was achieved with 45 mg/mL sodium ascorbate/5% ethanol only.

Initial labeling (radiolabeling step) can be achieved in the presence of sodium ascorbate.

Surprisingly, it was found that when labeling DOTATATE at lower temperatures, i.e. ≤30° C., chelation of Copper by DOTATATE occurs more rapidly than for other metals. This phenomenon can be used to reduce the quantity of metallic impurities present in the final drug product.

C. Preparation of the $^{64}$Cu-DOTATATE Bulk Solution i. Ligand

In one embodiment, the ligand is DOTATATE; 1,4,7,10-tetraazacyclododecane-1,4,7,10-tretraacetic acid (DOTA); 3,6,9,15-tetraazabicyclo [9.3.1]pentadeca-1(15),11,13-triene-3,6,9-triacetic acid (PCTA); 1,4,7-triazacyclononane-1,4,7-triyltriacetic acid (NOTA), or derivatives thereof.

In one embodiment, the ligand is add to the reaction mixture in an amount from about 1 μg to about 6000 μg, from about 50 μg to about 5000 μg, from about 100 μg to about 4500 μg, from about 200 μg to about 4000 μg, from about 300 μg to about 3000 μg, from about 400 μg to about 2000 μg, from about 500 μg to about 1000 μg. In another embodiment, the ligand is added to the reaction mixture in an amount of about 100 μg, about 200 μg, about 300 μg, about 400 μg, about 500 μg, about 600 μg, about 700 μg, about 800 μg, about 900 μg, about 1000 μg, about 1100 μg, about 1200 μg, about 1300 μg, about 1400 μg, about 1500 μg, about 1600 μg, about 1700 μg, about 1800 μg, about 1900 μg, about 2000 μg, 2100 μg, about 2200 μg, about 2300 μg, about 2400 μg, about 2500 μg, about 2600 μg, about 2700 μg, about 2800 μg, about 2900 μg, about 3000 μg, about 3100 μg, about 3200 μg, about 3300 μg, about 4400 μg, about 4500 μg, about 5000 μg, about 5500 μg, or about 6000 μg. In yet another embodiment, the ligand is added to the reaction mixture in an amount of less than about 100 μg, less than about 200 μg, less than about 300 μg, less than about 400 μg, less than about 500 μg, less than about 600 μg, less than about 700 μg, less than about 800 μg, less than about 900 μg, less than about 1000 μg, less than about 1100 μg, less than about 1200 μg, less than about 1300 μg, less than about 1400 μg, less than about 1500 μg, less than about 1600 μg, less than about 1700 μg, less than about 1800 μg, less than about 1900 μg, less than about 2000 μg, less than about 2100 μg, less than about 2200 μg, less than about 2300 μg, less than about 2400 μg, less than about 2500 μg, less than about 2600 μg, less than about 2700 μg, less than about 2800 μg, less than about 2900 μg, less than about 3000 μg, less than about 3100 μg, less than about 3200 μg, less than about 3300 μg, less than about 4400 μg, less than about 4500 μg, less than about 5000 μg, less than about 5500 μg, or less than about 6000 μg.

In another embodiment, the ligand is used in an amount from about 0.1 ug/mCi to about 20 ug/mCi, from about 0.5 ug/mCi to about 15 ug/mCi, from about 1 ug/mCi to about 11 ug/mCi, from about 1 ug/mCi to about 8 ug/mCi, from about 1 ug/mCi to about 5 ug/mCi, from about 1 ug/mCi to about 3 ug/mCi, or from about 0.1 ug/mCi to about 1.5 ug/mCi. In yet another embodiment, the ligand is used in an amount of about 0.1 ug/mCi, about 0.25 ug/mCi, about 0.4 ug/mCi, about 0.5 ug/mCi, about 0.6 ug/mCi, about 0.75 ug/mCi, about 0.8 ug/mCi, about 1 ug/mCi, about 1.25 ug/mCi, about 1.5 ug/mCi, about 1.75 ug/mCi, about 2 ug/mCi, about 2.5 ug/mCi, about 3 ug/mCi, about 3.5, or about 4 ug/mCi.

In one embodiment, the concentration of the ligand/mL in the radiolabeling step is great than about 200 ug/mL, greater than about 250 ug/mL, great than about 300 ug/mL, great than about 333 ug/mL, or great than about 400 ug/mL.

In yet another embodiment, the total ligand labeled is from about 200 μg to about 6000 μg, from about 500 μg to about 5000 µg, from about 1000 µg to about 4000 µg, from about 1500 µg to about 3000 µg, from about 2000 µg to about 25000 µg, from about 2000 µg to about 4000 µg, from about 3000 µg to about 4000 µg. In another embodiment, the total ligand labeled is about 200 µg, about 300 µg, about 400 µg, about 500 µg, about 600 µg, about 700 µg, about 800 µg, about 900 µg, about 1000 µg, about 1100 µg, about 1200 µg, about 1300 µg, about 1400 µg, about 1500 µg, about 1600 µg, about 1700 µg, about 1800 µg, about 1900 µg, about 2000 µg, 2100 µg, about 2200 µg, about 2300 µg, about 2400 µg, about 2500 jig, about 2600 µg, about 2700 µg, about 2800 µg, about 2900 µg, about 3000 µg, about 3100 µg, about 3200 µg, about 3300 µg, about 4000 µg, about 4500 µg, about 5000 µg, about 5500 µg, or about 6000 µg. In yet another embodiment, the total ligand labeled is less than about 500 µg, less than about 1000 µg, less than about 1500 µg, less than about 2000 µg, less than about 2500 µg, less than about 3000 µg, less than about 3500 µg, less than about 4000 µg, less than about 45000 µg, less than about 5000 µg, less than about 5500 µg, less than about 6000 µg, less than about 6500 µg, less than about 7000 µg, less than about 8000 µg, less than about 9000 µg, or less than about 10000 µg.

ii. Radionuclide

In another embodiment, the radionuclide is Bismuth-213, Chromium-51, Cobalt-60, Dysprosium-165, Erbium-169, Holmium-166, Iridium-192, Iron-59, Lead-212, Lutetium-177, Molybdenum-99, Palladium-103, Rhenium-186, Rhenium-188, Samarium-153, Strontium-89, Technetium-99m, Xenon-133, Ytterbium-169, Ytterbium-177, Yttrium-90, Carbon-11, Cobalt-57, Copper-64, Copper-67, Fluorine-18, Gallium-67, Gallium-68, Germanium-68, Indium-111, Rubidium-81, Rubidium-82, Strontium-82, Thallium-201 or the like.

In another embodiment, $^{64}CuCl_2$ is added to the reaction mixture (as a source of $^{64}Cu$) in an amount from about 100 mCi to about 5000 mCi, from about 200 mCi to about 4000 mCi, from about 300 mCi to about 3500 mCi, from about 400 mCi to about 3000 mCi, from about 500 mCi to about 2500 mCi, or in an amount up to about 10,000 mCi. In one embodiment, $^{64}CuCl_2$ is added to the reaction mixture (as a source of $^{64}Cu$) in an amount of about 100 mCi, about 200 mCi, about 300 mCi, about 400 mCi, about 500 mCi, about 600 mCi, about 700 mCi, about 800 mCi, about 900 mCi, about 1000 mCi, about 1500 mCi, about 2000 mCi, about 2500 mCi, about 3000 mCi, about 3500 mCi, about 4000 mCi, about 4500 mCi, about 5000 mCi, about 5500 mCi, about 6000 mCi, about 6500 mCi, about 7000 mCi, about 7500 mCi, about 8000 mCi, about 8500 mCi, about 9000 mCi, about 9500 mCi, or about 10,000 mCi. In yet another embodiment, $^{64}CuCl_2$ is added to the reaction mixture (as a source of $^{64}Cu$) in an amount of less than about 100 mCi, less than about 200 mCi, less than about 300 mCi, less than about 400 mCi, less than about 500 mCi, less than about 600 mCi, less than about 700 mCi, less than about 800 mCi, less than about 900 mCi, less than about 1000 mCi, less than about 1500 mCi, less than about 2000 mCi, less than about 2500 mCi, less than about 3000 mCi, less than about 3500 mCi, less than about 4000 mCi, less than about 4500 mCi, less than about 5000 mCi, less than about 5500 mCi, less than about 6000 mCi, less than about 6500 mCi, less than about 7000 mCi, less than about 7500 mCi, less than about 8000 mCi, less than about 8500 mCi, less than about 9000 mCi, less than about 9500 mCi, or less than about 10,000 mCi.

In one embodiment, the radionuclide is added to the reaction mixture in an amount of about of about 0.1 µg, about 0.2 µg, about 0.3 µg, about 0.39 µg, about 0.4 µg, about 0.44 µg, about 0.5 µg, about 0.6 µg, about 0.7 µg, about 0.8 µg, about 0.9 µg, about 1 µg, about 1.12 µg, about 2 µg, about 3 µg, about 4 µg, about 5 µg, about 6 µg, about 7 µg, about 8 µg, about 9 µg or about 10 µg.

In yet another embodiment, $^{64}Cu$ is added to the reaction mixture in an amount of about of about 0.1 µg, about 0.2 µg, about 0.3 µg, about 0.4 µg, about 0.44 µg, about 0.5 µg, about 0.6 µg, about 0.7 µg, about 0.8 µg, about 0.9 µg, about 1 µg, about 2 µg, about 3 µg, about 4 µg, about 5 µg, about 6 µg, about 7 µg, about 8 µg, about 9 µg or about 10 µg.

iii. Buffer Solution

In one embodiment, the buffer solution used in the preparation of the bulk solution of the drug product is sodium acetate buffer, sodium acetate/gentisic acid buffer, sodium ascorbate buffer, sodium ascorbate/ethanol buffer, ammonium acetate buffer, ammonium acetate/gentisic acid buffer, ammonium ascorbate buffer, ammonium ascorbate/ethanol buffer, or any other appropriate buffer.

In one embodiment, the concentration of the buffer is about 0.1M, about 0.2M, about 0.3 M, about. 4 M, about 0.5 M, about 0.6 M, about 0.7 M, about 0.8 M, about 0.9 M or about 1.0 M. In yet another embodiment, the concentration of the buffer is from about 20 mg/mL to about 200 mg/mL, from about 25 mg/mL to about 190 mg/mL, from about 30 mg/mL to about 170 mg/mL, from about 35 mg/mL to about 160 mg/mL, from about 40 mg/mL to about 150 mg/mL, from about 45 mg/mL to about 140 mg/mL, from about 45 mg/mL to about 122 mg/mL, from about 50 mg/mL to about 130 mg/mL, from about 60 mg/mL to about 120 mg/mL, or from about 70 mg/mL to about 100 mg/mL. In yet another embodiment, the concentration of the buffer is about 4 mg/mL, about 10 mg/mL, about 20 mg/mL, about 25 mg/mL, about 30 mg/mL, about 35 mg/mL, about 40 mg/mL, about 45 mg/mL, about 50 mg/mL, about 60 mg/mL, about 65% mg/mL, about 66% mg/mL, about 70 mg/mL, about 80 mg/mL, about 90 mg/mL, about 95%, about 100 mg/mL, about 110 mg/mL, about 120 mg/mL, about 122 mg/mL, about 130 mg/mL, about 132 mg/mL, about 140 mg/mL, about 150 mg/mL, about 160 mg/mL, about 170 mg/mL, about 180 mg/mL, about 190 mg/mL, or about 200 mg/mL.

In another embodiment, the buffer comprises about 4 mg/mL, about 10 mg/mL, about 15 mg/mL, about 20 mg/mL, about 25 mg/mL, about 30 mg/mL, about 35 mg/mL, about 40 mg/mL, about 45 mg/mL, about 50 mg/mL, about 60 mg/mL, about 70 mg/mL, about 80 mg/mL, about 90 mg/mL or about 100 mg/mL gentisic acid and about 0.1M, about 0.2M, about 0.3 M, about 0.33M, about 0.4 M, about 0.5 M, about 0.6 M, about 0.7 M, about 0.8 M, about 0.9 M or about 1.0 M of sodium acetate.

In one specific embodiment, the buffer is a solution of 4 mg/mL of gentisic acid and 0.4 M of sodium acetate.

In yet another embodiment, the buffer comprises about 4 mg/mL, about 10 mg/mL, about 20 mg/mL, about 25 mg/mL, about 30 mg/mL, about 35 mg/mL, about 40 mg/mL, about 45 mg/mL, about 46% mg/mL, about 50 mg/mL, about 60 mg/mL, about 64.8 mg/mL, about 66% mg/mL, about 70 mg/mL, about 80 mg/mL, about 90 mg/mL, about 100 mg/mL sodium ascorbate and about 1%, about 2%, about 2.8%, about 3%, about 3.5%, about 4%, about 5%, about 8%, about 10%, about 15%, about 20%, about 25% or about 30% of EtOH. In one specific embodiment, the buffer is a solution having 45 mg/mL of sodium ascorbate and 5% EtOH.

In another embodiment, the buffer comprises about 4 mg/mL, about 10 mg/mL, about 15 mg/mL, about 20 mg/mL, about 25 mg/mL, about 30 mg/mL, about 35 mg/mL, about 40 mg/mL, about 45 mg/mL, about 50 mg/mL, about 60 mg/mL, about 70 mg/mL, about 80 mg/mL, about 90 mg/mL or about 100 mg/mL gentisic acid and about 0.1M, about 0.2M, about 0.3 M, about 0.33M, about 0.4 M, about 0.5 M, about 0.6 M, about 0.7 M, about 0.8 M, about 0.9 M or about 1.0 M of sodium ascorbate.

iv. Stabilizer

In one embodiment the stabilizer is gentisic acid. In another embodiment, the stabilizer is sodium ascorbate. However, any appropriate stabilizer may be used.

In another embodiment, more than one stabilizer is used. In one embodiment, one stabilizer, such as gentisic acid, is used during the radiolabeling process, and another stabilizer, such as sodium ascorbate, is used in the final formulated product.

In one embodiment, stabilizer is added in an amount of about 1.0 g to about 9.0 g. In one embodiment, stabilizer is added in an amount of about 2.0 mg to about 8.0 mg. In another embodiment, stabilizer is added in an amount of about 3.0 mg to about 7.0 mg. In another embodiment, stabilizer is added in an amount of about 3.0 mg to about 5.0 mg. In another embodiment, stabilizer is added in an amount of about 4.0 mg to about 6.0 mg. In one specific embodiment, stabilizer is added in an amount of about 4.0 mg to the reaction mixture.

In yet another embodiment, the stabilizer is added in an amount of about 1.0 g to about 9.0 g. In another embodiment, gentisic acid is added in an amount of about 2.0 mg to about 8.0 mg. In another embodiment, gentisic acid is added in an amount of about 3.0 mg to about 7.0 mg. In another embodiment, gentisic acid is added in an amount of about 3.0 mg to about 5.0 mg. In another embodiment, gentisic acid is added in an amount of about 4.0 mg to about 6.0 mg. In one specific embodiment, gentisic acid is added in an amount of about 4.0 mg to the reaction mixture.

In another embodiment, sodium ascorbate is added in an amount of about 2.0 mg to about 8.0 mg. In another embodiment, sodium ascorbate is added in an amount of about 3.0 mg to about 7.0 mg. In another embodiment, sodium ascorbate is added in an amount of about 3.0 mg to about 5.0 mg. In another embodiment, sodium ascorbate is added in an amount of about 4.0 mg to about 6.0 mg. In one specific embodiment, sodium ascorbate is added in an amount of about 4.0 mg to the reaction mixture.

v. Radiolabeling Conditions

In one embodiment, radiolabeling is performed at 500 mCi to 15,000 mCi of radionuclide. Radioactive concentration at radiolabeling is ≥250 mCi/mL, ≥3 00 ug/mL, ≥333 mCi/mL, ≥350 mCi/mL, ≥400 mCi/mL, ≥421 mCi/mL or ≥460 mCi/mL. The total ligand labeled is 1000-4000 ug or a concentration of ≥333 ug/mL.

In one embodiment, radiolabeling is performed at 500 mCi to 10,000 mCi of radionuclide. Radioactive concentration at radiolabeling is ≥333 mCi/mL. The total ligand labeled is 1000-4000 ug or a concentration of ≥333 ug/mL.

In another embodiment, radiolabeling is performed at 500 mCi to 2,500 mCi of radionuclide. Radioactive concentration at radiolabeling is ≥250 mCi/mL, ≥300 ug/mL, ≥333 mCi/mL, ≥350 mCi/mL, ≥400 mCi/mL, ≥421 mCi/mL or ≥460 mCi/mL. Total ligand labeled is 1000-4000 µg or a concentration of ≥333 µg/mL.

In one embodiment, radiolabeling is performed at 500 mCi to 15,000 mCi $^4$Cu. Radioactive concentration at radiolabeling is ≥250 mCi/mL, ≥300 mL, ≥333 mCi/mL, ≥350 ug/mL, ≥400 mCi/mL, ≥421 mCi/mL or ≥460 mCi/mL. The total DOTATATE labeled is 1000-4000 ug or a concentration of ≥333 ug/mL.

In one embodiment, radiolabeling is performed at 500 mCi to 10,000 mCi 64Cu. Radioactive concentration at radiolabeling is ≥333 mCi/mL. The total DOTATATE labeled is 1000-4000 ug or a concentration of ≥333 ug/mL.

In another embodiment, radiolabeling is performed at 500 mCi to 2,500 mCi $^{64}$Cu. Radioactive concentration at radiolabeling is ≥250 mCi/mL, ≥300 ug/mL, ≥333 mCi/mL, ≥350 ug/mL, ≥400 mCi/mL, ≥421 mCi/mL or ≥460 mCi/mL. Total DOTATATE labeled is 1000-4000 µg or a concentration of ≥333 µg/mL.

In another embodiment, the pH of the reaction mixture is 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9 or 7.0. In yet another embodiment, the pH of the reaction mixture is from about 4.5 to about 7.0, from about 4.6 to about 6.9, from about 4.7 to about 6.8, from about 4.8 to about 6.7, from about 4.9 to about 6.6, from about 5.0 to about 6.6, from about 5.1 to about 6.5, from about 5.2 to about 6.3, from about 5.3 to about 6.2, from about 5.4 to about 6.1, or from about 5.5 to about 6.0. In one specific embodiment, the pH of the reaction mixture is from about 5 to about 6.

Bioconjugate chelates such as DOTA-TATE are commonly complexed at temperatures from 50 to 95° C. to ensure high radiochemical labeling and radiolabeling yield. However, the current disclosure teaches that by labeling at lower temperatures, i.e. room temperature or lower, the purity of the copper $^{64}$Cu-DOTATATE is improved due to the more rapid labeling of the copper (2+) ion to the DOTATATE compared to other common metal impurities.

In another embodiment, the temperature of the reaction mixture is from about 10° C. to about 50° C., from about 15° C. to about 45° C., from about 20° C. to about 40° C., from about 10° C. to about 30° C., from about 10° C. to about 20° C., from about 20° C. to about 50° C., from about 20° C. to about 40° C., or from about 20° C. to about 30° C. In one embodiment, the temperature of the reaction mixture is about 10° C., about 15° C., about 20° C., about 22° C., about 25° C., about 30° C., about 35° C., about 40° C., about 45° C., or about 50° C. In another embodiment, the temperature of the reaction mixture is ambient temperature.

In yet another embodiment, the temperature of the reaction mixture is less than or equal to 50° C., is less than 50° C., is less than or equal to 45° C., is less than 45° C., is less than or equal to 40° C., is less than 40° C., is less than or equal to 35° C., is less than 35° C., is less than or equal to 30° C., is less than 30° C., is less than or equal to 25° C., is less than 25° C., is less than or equal to 20° C., is less than 20° C., is less than or equal to 15° C., is less than 15° C., is less than or equal to 10° C., or is less than 10° C.

In one embodiment, the molar ratio of ligand to radionuclide in the reaction mixture is about 125:1, 120:1, 115:1, 110:1, 105:1, 100:1, 95:1, 90:1, 85:1, 80:1, 75:1, 70:1, 65:1, 60:1, 55:1, 50:1, 45:1, 40:1, 35:1, 30:1, 25:1, 20:1, 15:1, 10:1, 5:1, 4:1, 3:1, 2:1, 2.5:1, or 1:1. In another embodiment, the molar ratio of ligand to radionuclide in the reaction mixture is about 125:1 to about 75:1. In still another embodiment, the mole ratio of ligand to radionuclide in the reaction mixture is about 105:1 to about 95:1. In still another embodiment, the mole ratio of ligand to radionuclide in the reaction mixture is about 110:1 to about 90:1. In still another embodiment, the mole ratio of ligand to radionuclide in the reaction mixture is about 102:1 to about 99:1. In yet another embodiment, the mole ratio of ligand to radionuclide in the reaction mixture is about 125:1 to about 1:1, about 105:1 to about 10:1, about 102:1 to about 10:1, about 110:1 to about 50:1, about 90:1 to about 70:1, or about 60:1 to about 1:1, or about 110:1 to about 90:1, In one specific embodiment, the mole ratio of DOTATATE to $^{64}$Cu is about 125:1, 120:1, 115:1, 110:1, 105:1, 100:1, 95:1, 90:1, 85:1, 80:1, 75:1, 70:1, 65:1, 60:1, 55:1, 50:1, 45:1, 40:1, 35:1, 30:1, 25:1, 20:1, 15:1, 10:1, 5:1, 4:1, 3:1, 2:1, 2.5:1, or 1:1. In another embodiment, the mole ratio of DOTATATE to $^{64}$Cu in the reaction mixture is about 105:1 to about 95:1. In still another embodiment, the mole ratio of DOTATATE to $^{64}$Cu in the reaction mixture is about 102:1 to about 99:1. In yet another embodiment, the mole ratio of DOTATATE to $^{64}$Cu in the reaction mixture is about 125:1 to about 1:1, about 105:1 to about 10:1, about 102:1 to about 10:1, about 110:1 to about 50:1, about 90:1 to about 70:1, or about 60:1 to about 1:1, or about 110:1 to about 90:1, In one embodiment, the mass of ligand (µg): radioactivity of radionuclide (mCi) ratio is about 5:1, 4:1, 3:1, 2:1, or 1:1. In yet another embodiment, the mass of ligand (µg) to radioactivity of radionuclide (mCi) concentration is about 1.0 µg/mCi, 0.9 µg/mCi, 0.8 µg/mCi, 0.7 µg/mCi, 0.6 µg/mCi, 0.5 µg/mCi, 0.4 µg/mCi, 0.3 µg/mCi, 0.2 µg/mCi, or 0.1 µg/mCi for each reaction. In still another embodiment, the mass of ligand (µg) to radioactivity of radionuclide (mCi) concentration was about 0.6 µg/mCi for each reaction.

In one embodiment, the mass of ligand (µg): radioactivity of $^{64}$Cu (mCi) ratio is about 5:1, 4:1, 3:1, 2:1, or 1:1. In yet another embodiment, the mass of ligand (µg) to radioactivity of $^{64}$Cu (mCi) concentration is about 1.0 µg/mCi, 0.9 µg/mCi, 0.8 µg/mCi, 0.7 µg/mCi, 0.6 µg/mCi, 0.5 µg/mCi, 0.4 µg/mCi, 0.3 µg/mCi, 0.2 µg/mCi, or 0.1 µg/mCi for each reaction. In still another embodiment, the mass of ligand (µg) to radioactivity of $^{64}$Cu (mCi) concentration was about 0.6 µg/mCi for each reaction.

In one embodiment, the mass of DOTATATE (µg): radioactivity of $^{64}$Cu (mCi) ratio is about 5:1, 4:1, 3:1, 2:1, or 1:1. In yet another embodiment, the mass of DOTATATE (µg) to radioactivity of $^{64}$Cu (mCi) concentration is about 1.0 µg/mCi, 0.9 µg/mCi, 0.8 µg/mCi, 0.7 µg/mCi, 0.6 µg/mCi, 0.5 µg/mCi, 0.4 µg/mCi, 0.3 µg/mCi, 0.2 µg/mCi, or 0.1 µg/mCi for each reaction. In still another embodiment, the mass of DOTATATE (µg) to radioactivity of $^{64}$Cu (mCi) concentration was about 0.6 µg/mCi for each reaction.

In one embodiment, the radioactivity of the bulk solution of the drug substance is from about 1 mCi to about 10,000 mCi, from about 1 mCi to about 9,900 mCi, from about 1 mCi to about 9,800 mCi, from about 1 mCi to about 9,700 mCi, from about 1 mCi to about 9,600 mCi, from about 1 mCi to about 9,500 mCi, from about 1 mCi to about 9,400 mCi, from about 1 mCi to about 9,300 mCi, from about 1 mCi to about 9,200 mCi, from about 1 mCi to about 9,100 mCi, from about 1 mCi to about 9,000 mCi, from about 1 mCi to about 8,900 mCi, from about 1 mCi to about 8,800 mCi, from about 1 mCi to about 8,700 mCi, from about 1 mCi to about 8,600 mCi, from about 1 mCi to about 8,500 mCi, from about 1 mCi to about 8,400 mCi, from about 1 mCi to about 8,300 mCi, from about 1 mCi to about 8,200 mCi, from about 1 mCi to about 8,100 mCi, from about 1 mCi to about 8,000 mCi, from about 1 mCi to about 7,900 mCi, from about 1 mCi to about 7,800 mCi, from about 1 mCi to about 7,700 mCi, from about 1 mCi to about 7,600 mCi, from about 1 mCi to about 7,500 mCi, from about 1 mCi to about 7,400 mCi, from about 1 mCi to about 7,300 mCi, from about 1 mCi to about 7,200 mCi, from about 1 mCi to about 7,100 mCi, from about 1 mCi to about 7,000 mCi, from about 1 mCi to about 6,900 mCi, from about 1 mCi to about 6,800 mCi, from about 1 mCi to about 6,700 mCi, from about 1 mCi to about 6,600 mCi, from about 1 mCi to about 6,500 mCi, from about 1 mCi to about 6,400 mCi, from about 1 mCi to about 6,300 mCi, from about 1 mCi to about 6,200 mCi, from about 1 mCi to about 6,100 mCi, from about 1 mCi to about 6,000 mCi, from about 1 mCi to about 5,900 mCi, from about 1 mCi to about 5,800 mCi, from about 1 mCi to about 5,700 mCi, from about 1 mCi to about 5,600 mCi, from about 1 mCi to about 5,500 mCi, from about 1 mCi to about 5,400 mCi, from about 1 mCi to about 5,300 mCi, from about 1 mCi to about 5,200 mCi, from about 1 mCi to about 5,100 mCi, from about 1 mCi to about 5,000 mCi, from about 1 mCi to about 4,900 mCi, from about 1 mCi to about 4,800 mCi, from about 1 mCi to about 4,700 mCi, from about 1 mCi to about 4,600 mCi, from about 1 mCi to about 4,500 mCi, from about 1 mCi to about 4,400 mCi, from about 1 mCi to about 4,300 mCi, from about 1 mCi to about 4,200 mCi, from about 1 mCi to about 4,100 mCi, from about 1 mCi to about 4,000 mCi, from about 1 mCi to about 3,900 mCi, from about 1 mCi to about 3,800 mCi, from about 1 mCi to about 3,700 mCi, from about 1 mCi to about 3,600 mCi, from about 1 mCi to about 3,500 mCi, from about 1 mCi to about 3,400 mCi, from about 1 mCi to about 3,300 mCi, from about 1 mCi to about 3,200 mCi, from about 1 mCi to about 3,100 mCi, from about 1 mCi to about 3000 mCi, from about 10 mCi to about 2900 mCi, from about 20 mCi to about 2,800 mCi, from about 30 mCi to about 2,700 mCi, from about 40 mCi to about 2,600 mCi, from about 50 mCi to about 2,500 mCi, from about 60 mCi to about 2,400 mCi, from about 70 mCi to about 2,300 mCi, from about 80 mCi to about 2200 mCi, from about 90 mCi to about 2,100 mCi, from about 100 mCi to about 2,000 mCi, from about 150 mCi to about 3000 mCi, from about 200 mCi to about 2500 mCi, from about 250 mCi to about 2,000 mCi, from about 300 mCi to about 1,500 mCi, from about 400 mCi to about 1,000 mCi, or from about 500 mCi to about 750 mCi.

In another embodiment, the radioactivity of the bulk solution of the drug substance is about 1 mCi, about 20 mCi, about 40 mCi, about 60 mCi, about 80 mCi, about 100 mCi, about 120 mCi, about 140 mCi, about 160 mCi, about 200 mCi, about 220 mCi, about 240 mCi, about 260 mCi, about 280 mCi, about 300 mCi, about 320 mCi, about 340 mCi, about 360 mCi, about 380 mCi, about 400 mCi, about 420 mCi, about 440 mCi, about 460 mCi, about 480 mCi, about 500 mCi, about 550 mCi, about 600 mCi, about 650 mCi, about 700 mCi, about 750 mCi, about 800 mCi, about 850 mCi, about 900 mCi, about 950 mCi, about 1,000 mCi, about 1,100 mCi, about 1,200 mCi, about 1,300 mCi, about 1,400 mCi, about 1,500 mCi, about 1,600 mCi, about 1,700 mCi, about 1,800 mCi, about 1,900 mCi, about 2,000 mCi, about 2,100 mCi, about 2,200 mCi, about 2,300 mCi, about 2,400 mCi, about 2,500 mCi, about 2,600 mCi, about 2,700 mCi, about 2,800 mCi, about 2,900 mCi, about 3,000 mCi, about 3,100 mCi, about 3,200 mCi, about 3,300 mCi, about 3,400 mCi, about 3,500 mCi, about 3,600 mCi, about 3,700 mCi, about 3,800 mCi, about 3,900 mCi, about 4,000 mCi, about 4,100 mCi, about 4,200 mCi, about 4,300 mCi, about 4,400 mCi, about 4,500 mCi, about 4,600 mCi, about 4,700 mCi, about 4,800 mCi, about 4,900 mCi, about 5,000 mCi, about 5,100 mCi, about 5,200 mCi, about 5,300 mCi, about 5,400 mCi, about 5,500 mCi, about 5,600 mCi, about 5,700 mCi, about 5,800 mCi, about 5,900 mCi, about 6,000 mCi, about 6,100 mCi, about 6,200 mCi, about 6,300 mCi, about 6,400 mCi, about 6,500 mCi, about 6,600 mCi, about 6,700 mCi, about 6,800 mCi, about 6,900 mCi, about 7,000 mCi, about 7,100 mCi, about 7,200 mCi, about 7,300 mCi, about 7,400 mCi, about 7,500 mCi, about 7,600 mCi, about 7,700 mCi, about 7,800 mCi, about 7,900 mCi, about 8,000 mCi, about 8,100 mCi, about 8,200 mCi, about 8,300 mCi, about 8,400 mCi, about 8,500 mCi, about 8,600 mCi, about 8,700 mCi, about 8,800 mCi, about 8,900 mCi, about 9,000 mCi, 9,100 mCi, about 9,200 mCi, about 9,300 mCi, about 9,400 mCi, about 9,500 mCi, about 9,600 mCi, about 9,700 mCi, about 9,800 mCi, about 9,900 mCi, or about 10,000 mCi, In one specific embodiment, the radioactivity of the bulk solution of the drug substance is about 100 mCi, 500 mCi, 1000 mCi, 2000 mCi, 3,000 mCi, 4,000, mCi, 5,000 mCi, 6,000 mCi, 7,000 mCi, 8,000 mCi, 9,000 mCi, or 10,000 mCi.

In one embodiment, the volume of radionuclide solution is from about 0.1 mL to about 10 mL, from about 0.2 mL to about 9 mL, from about 0.3 mL to about 8 mL, from about 0.4 mL to about 7 mL, from about 0.5 mL to about 6 mL, from about 1 mL to about 5 mL, from about 2 mL to about 4 mL. In another embodiment, the volume of radionuclide solution is about 0.1 mL, about 0.2 mL, about 0.3 mL, about 0.4 mL, about 0.5 mL, about 1 mL, about 2 mL, about 3 mL, about 4 mL, about 5 mL, about 6 mL, about 7 mL, about 8 mL, about 9 mL, or about 10 mL. In one embodiment, the volume of $^{64}$Cu solution is from about 0.1 mL to about 10 mL, from about 0.2 mL to about 9 mL, from about 0.3 mL to about 8 mL, from about 0.4 mL to about 7 mL, from about 0.5 mL to about 6 mL, from about 1 mL to about 5 mL, from about 2 mL to about 4 mL. In another embodiment, the volume of $^{64}$Cu solution is about 0.1 mL, about 0.2 mL, about 0.3 mL, about 0.4 mL, about 0.5 mL, about 1 mL, about 2 mL, about 3 mL, about 4 mL, about 5 mL, about 6 mL, about 7 mL, about 8 mL, about 9 mL, or about 10 mL.

In yet another embodiment, the volume in radiolabeling solution is from about 0.1 mL to about 10 mL, from about 0.5 mL to about 9 mL, from about 1 mL to about 7 mL, from about 1.5 mL to about 6 mL, from about 0.5 mL to about 6 mL, from about 1 mL to about 5 mL, from about 2 mL to about 4 mL. In another embodiment, the volume in radiolabeling solution is about 0.1 mL, about 0.2 mL, about 0.3 mL, about 0.4 mL, about 0.5 mL, about 1 mL, about 1.5 mL, about 2 mL, about 3 mL, about 4 mL, about 5 mL, about 6 mL, about 7 mL, about 8 mL, about 9 mL, or about 10 mL.

In another embodiment, the reaction time is about 1 mm, about 2 mm, about 3 mm, about 4 min, about 5 min, about 6 min, about 7 min, about 8 min, about 9 min, about 10 min, about 15 min, about 20 min, about 25 min, about 30 min, about 45 min, about 1 hr, about 2 hr, about 3 hr, about 4 hr, about 5 hr, about 6 hr, about 7 hr, about 8 hr, about 9 hr, or about 10 hr. In one embodiment, the reaction time is from about 1 min to about 24 hr, from about 1 min to about 18 hr, from about 1 min to about 12 hr, or from about 1 min to about 6 hr. In yet another embodiment, the reaction time is from about 1 min to about 60 min, from about 2 min to about 45 min, or from about 5 min to about 30 min.

In yet another embodiment, the concentration of anti-radiolysis agent in final formulation is 29-122 mg/mL+1-5% ethanol.

In still another embodiment, the amount of non-radioactive copper added to the reaction mixture is 0-30 µg/mL (ppm). In yet another embodiment, the amount of non-radioactive copper added to the reaction mixture is 0.1-30 µg/mL (ppm).

D. Purification of the 64Cu-DOTATATE Bulk Solution

In yet another embodiment, the bulk metal-ligand solution is purified using C-18 Light Sep Pak or any appropriate purification system/column.

In on embodiment, elution solvent in purification is ethanol, 5% ethanol (95% water), 10% ethanol (90% water), 15% ethanol (85% water), 20% ethanol (80% water), 25% ethanol (75% water), 30% ethanol (70% water), 35% ethanol (65% water), 40% ethanol (60% water), 45% ethanol (55% water), 50% ethanol (50% water), 55% ethanol (45% water), 60% ethanol (40% water), 65% ethanol (35% water), 70% ethanol (30% water), 75% ethanol (25% water), 80% ethanol (20% water), 85% ethanol (15% water), 90% ethanol (10% water), 95% ethanol (5% water), or 100% ethanol.

In yet another embodiment, the volume of solvent from purification step is from about 0.1 mL to about 10 mL, from about 0.5 mL to about 9 mL, from about 1 mL to about 7 mL, from about 1.5 mL to about 6 mL, from about 0.5 mL to about 6 mL, from about 1 mL to about 5 mL, from about 2 mL to about 4 mL. In another embodiment, the volume of solvent from purification step is about 0.1 mL, about 0.2 mL, about 0.3 mL, about 0.4 mL, about 0.5 mL, about 1 mL, about 1.5 mL, about 2 mL, about 3 mL, about 4 mL, about 5 mL, about 6 mL, about 7 mL, about 8 mL, about 9 mL, or about 10 mL.

In another embodiment, the radionuclidic purity of $^{64}$Cu in the drug product is ≥99%, ≥99.1%, ≥99.2%, ≥99.3%, ≥99.4%, ≥99.5%, ≥99.6%, ≥99.7%, ≥99.8%, or ≥99.9%.

In yet another embodiment, the quantity of radionuclidic impurities in the drug product is 1%, ≤0.9%, ≤0.8%, ≤0.7%, ≤0.6%, ≤0.5%, ≤0.4%, ≤0.3%, ≤0.2%, or ≤0.1%. In another embodiment, quantity of one single radionuclidic impurity in the drug product is ≤0.1%, ≤0.09%, ≤0.08%, ≤0.07%, ≤0.06%, ≤0.05%, ≤0.04%, ≤0.03%, ≤0.02%, or ≤0.01%.

In one embodiment, the radiochemical purity of the drug product is ≥90%, ≥91%, ≥92%, ≥93%, ≥94%, ≥95%, ≥96%, ≥97%, ≥98%, ≥99%, ≥99.1%, ≥99.2%, ≥99.3%, 99.4%, ≥99.5%, ≥99.6%, ≥99.7%, ≥99.8%, or ≥99.9% as Copper Cu 64 DOTATATE.

In one embodiment, the purity is measured using High Performance Liquid Chromatograph (HPLC) or any other acceptable or appropriate techniques.

In another embodiment, gentisic acid is present in an amount of ≤50 ppm, ≤40 ppm, ≤30 ppm, ≤20 ppm, ≤10 ppm, ≤5 ppm, or ≤1 ppm in the drug product.

In one embodiment, a single impurity is present in an amount of ≤1%, ≤0.9%, ≤0.8%, ≤0.7%, ≤0.6%, ≤0.5%, ≤0.4%, ≤0.3%, ≤0.2%, or ≤0.1% of DOTATATE and related substances in the drug product.

In another embodiment, the total impurities are present in an amount of ≤10%, ≤9%, ≤8%, 7%, ≤6%, ≤5%, ≤4%, 3%, ≤2%, ≤1%, 0.9%, ≤0.8%, ≤0.7%, ≤0.6%, ≤0.5%, ≤0.4%, ≤0.3%, ≤0.2%, or ≤0.1% of DOTATATE and related substances in the drug product.

In another embodiment, bacterial endotoxins are present in the drug product in an amount of ≤100 EU/mL, ≤90 EU/mL, ≤80 EU/mL, ≤70 EU/mL, ≤60 EU/mL, ≤50 EU/mL, ≤40 EU/mL, ≤39 EU/mL, ≤30 EU/mL, ≤20 EU/mL, ≤10 EU/mL, ≤9 EU/mL, ≤8 EU/mL, ≤7 EU/mL, ≤6 EU/mL, ≤5 EU/mL, ≤4 EU/mL, ≤3 EU/mL, ≤2 EU/mL, or ≤1 EU/mL.

F. The Drug Product ($^{64}$Cu-DOTATATE Injection)

The drug product disclosed herein is indicated for use with positron emission tomography (PET) for localization of somatostatin receptor positive neuroendocrine tumors (NETs) in adult patients.

i. Chemical Characteristics

The drug Product described herein contains copper $^{64}$Cu-DOTATATE, which is a radioactive diagnostic drug for use with PET imaging. Chemically, $^{64}$Cu-DOTATATE is described as copper (Cu64)-N-[(4,7,10-Tricarboxymethyl-1,4,7,10-tetraazacyclododec-1-yl) acetyl]-Dphenylalanyl-L-cysteinyl-L-tyrosyl-D-tryptophanyl-L-lysyl-L-threoninyl-L-cysteinyl-L-threonine-cyclic (2-7) disulfide. The molecular weight is 1497.2 Daltons and the following is the structural formula in one isomeric form:

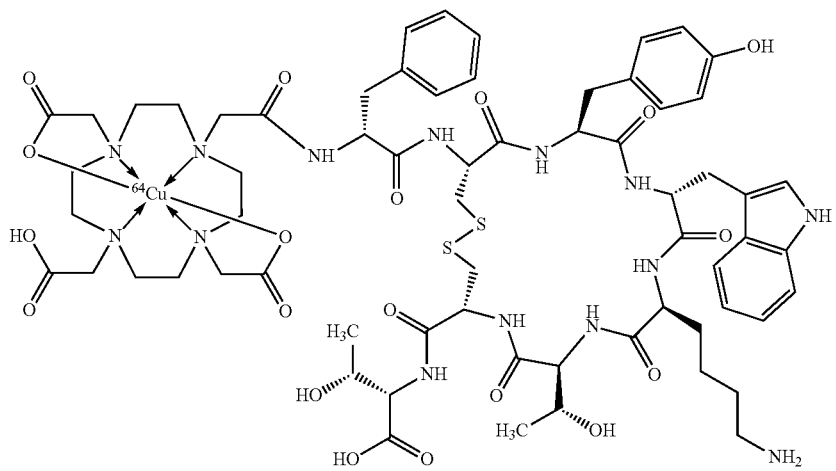

The drug product is a sterile, clear, colorless to yellow solution for intravenous use. Each 10 mL single-dose vial contains 148 MBq (4 mCi) of $^{64}$Cu-DOTATATE at calibration date and time in 4 mL solution volume. Additionally, each mL of the solution contains 40 mg ascorbic acid, 0.05 ml of dehydrated alcohol, USP (ethanol) in sterile water for injection, USP. The pH is adjusted with sodium hydroxide, hydrochloric acid and is between about 5.5 to 7.5.

ii. Physical Characteristics

Table 1 and Table 2 provide the principal radiation emission data and physical decay of $^{64}$Cu. $^{64}$Cu decays with a half-life $t_{1/2}$=12.7 hours via a combination of: (a) 17.6% positron emission to $^{64}$Ni, which results in emission of two 511 keV annihilation photons (35.7%), (b) 38.5% by beta decay to $^{64}$Zn, and (c) 43.8% by electron capture to $^{64}$Ni. Decay of Cu-64 also results in emission of a characteristic 1346 keV gamma ray with an intensity of about 0.48%

The gamma emission spectra of the drug product show peaks at about 511 keV and about 1346 keV.

TABLE 1

Principal radiation emission data (>1%)

| Radiation/Emission | % Disintegration | Mean Energy (keV) |
| --- | --- | --- |
| Positron ($\beta^+$) | 17.6 | 278 |
| Beta ($\beta^-$) | 38.5 | 190.7 |
| Gamma ($\gamma$) | 35.7 | 511 (annihilation) |
|  | 0.48 | 1346 |

TABLE 2

Physical decay chart of $^{64}$Cu

| Hours | Fraction Remaining |
| --- | --- |
| 0 | 1.00 |
| 1 | 0.947 |
| 3 | 0.849 |
| 6 | 0.721 |
| 9 | 0.612 |
| 12 | 0.520 |
| 18 | 0.374 |
| 24 (1 day) | 0.270 |
| 36 (1.5 days) | 0.140 |

TABLE 2-continued

Physical decay chart of $^{64}$Cu

| Hours | Fraction Remaining |
| --- | --- |
| 48 (2 days) | 0.073 |
| 72 (3 days) | 0.020 |
| 96 (4 days) | 0.005 | iii. External Radiation

Gamma constant: $3.6 \times 10^{-5}$ mSv/hr per MBq at 1 meter (0.133 mrem/hr per mCi at 1 meter). Table 3 displays the radiation attenuation by lead shielding of $^{64}$Cu.

TABLE 3

Radiation attenuation of $^{64}$Cu by lead shielding

| Shield Thickness cm of Lead (Pb) | Coefficient of Attenuation |
| --- | --- |
| 0.51 | 0.5 |
| 1.60 | 0.1 |
| 3.45 | 0.01 |
| 6.83 | 0.001 |

In one embodiment, the drug product is stored at a temperature from about 15° C. to about 30° C., from about 15° C. to about 25° C., from about 15° C. to about 20° C., or from about 20° C. to about 30° C. In another embodiment, the drug product is stored at a temperature of about 10° C., about 15° C., about 20° C., about 22° C., about 25° C., or about 30° C. In yet another embodiment, the drug product is stored at a controlled room temperature from about 20° C. to about 25° C.

In another embodiment, the drug product is stored at a temperature from about 30° C. to about 60° C., from about 35° C. to about 55° C., from about 40° C. to about 50° C., or from about 50° C. to about 60° C. In another embodiment, the drug product is stored at a temperature of about 30° C., about 35° C., about 40° C., about 45° C., about 50° C., about 55° C., or about 60° C. In yet another embodiment, the drug product is stored at a temperature from about 50° C. to about 55° C.

The radiochemical identity can be confirmed using HPLC. The HPLC Relative Retention Time (RRT) of $^{64}$Cu-DOTATATE correlates to that of DOTATATE standard. In one embodiment, the HPLC RRT of $^{64}$Cu-DOTATATE is from about 1 to about 2, or from about 1.15 to about 1.25.

The radionuclidic identity can be confirmed using gamma emission spectroscopy. The gamma emission spectra of the drug product shows peaks at about 511 keV and about 1346 keV.

In one embodiment, the solution volume of the drug product is from about 1 mL to about 10 mL, from about 2 mL to about 9 mL, from about 3 mL to about 7 mL, from about 4 mL to about 6 mL, or from about 3 mL to about 6 mL. In yet another embodiment, the solution volume of the drug product is about 1 mL, about 2, mL, about 3 mL, about 4 mL, about 5 mL, about 6 mL, about 7 mL, about 8 mL, about 9 mL or about 10 mL.

In yet another embodiment, the drug product is sterile, clear, colorless to yellow solution in a single-dose vial containing 148 MBq (4 mCi) (37 MBq (1 mCi) per 1 mL) of $^{4}$Cu-DOTATATE at calibration date and time. The sealed vial is contained in a shielded (lead) container for radiation protection. The drug product is shipped in a Type A package.

In one embodiment, the Total Vial Radioactivity (Assay) is from about 1.0 mCi/vial to about 10 mCi/vial, from about 1.5 mCi/vial to about 9 mCi/vial, from about 2.0 mCi/vial to about 8 mCi/vial, from about 2.5 mCi/vial to about 7 mCi/vial, from about 3.0 mCi/vial to about 6 mCi/vial, or from about 3.6 mCi/vial to about 4.4 mCi/vial. In another embodiment, the Total Vial Radioactivity (Assay) is about 1.0 mCi/vial, about 1.5 mCi/vial, about 2.0 mCi/vial, about 2.5 mCi/vial, about 3.0 mCi/vial, about 3.5 mCi/vial, about 3.6 mCi/vial, about 4.0 mCi/vial, about 4.4 mCi/vial, about 4.5 mCi/vial, about 5.0 mCi/vial, about 5.5 mCi/vial, about 6 mCi/vial, about 7 mCi/vial, about 8 mCi/vial, about 9 mCi/vial or about 10 mCi/vial.

In yet another embodiment, the radioactive concentration of the drug product is from about 0.5 mCi/mL to about 15 mCi/mL, from about 0.5 mCi/mL to about 12.5 mCi/mL, from about 0.5 mCi/mL to about 10 mCi/mL, from about 0.5 mCi/mL to about 7.5 mCi/mL, from about 0.5 mCi/mL to about 5 mCi/mL, from about 0.5 mCi/mL to about 3 mCi/mL, from about 0.6 mCi/mL to about 2.5 mCi/mL, from about 0.7 mCi/mL to about 2.0 mCi/mL, from about 0.8 mCi/mL to about 1.5 mCi/mL, or from about 0.9 mCi/mL to about 1.1 mCi/mL. In still another embodiment, the radioactive concentration of the drug product is about 15 mCi/mL, about 14 mCi/mL, about 13 mCi/mL, about 12 mCi/mL, about 11 mCi/mL, about 10 mCi/mL, about 9 mCi/mL, about 8 mCi/mL, about 7 mCi/mL, about 6 mCi/mL, or about 5 mCi/mL. In another embodiment, the radioactive concentration of the drug product is about 5-15 mCi/mL. In a further embodiment, the radioactive concentration of the drug product is about 9-14 mCi/mL. In yet another embodiment, the radioactive concentration of the drug product is about 10-11 mCi/mL. In still another embodiment, the radioactive concentration of the drug product is about 11-12 mCi/mL. In an additional embodiment, the radioactive concentration of the drug product is about 12-13 mCi/mL In another embodiment, the DOTATATE and related substances are present in an amount of ≤50 ppm, ≤40 ppm, ≤30 ppm, ≤27 ppm, ≤22.7 ppm, ≤20 ppm, or ≤10 ppm in the drug product.

In one embodiment, the Apparent Specific Activity of the drug product is ≥10 mCi/mg, ≥20 mCi/mg, ≥30 mCi/mg, ≥40 mCi/mg, ≥50 mCi/mg, ≥60 mCi/mg, ≥70 mCi/mg, ≥80 mCi/mg, or ≥90 mCi/mg DOTATATE and related substances at time of calibration.

In another embodiment, the average specific activity of the drug product is about 2.96 MBq/µg. In another embodiment, the average specific activity of the drug product is from about 1.0 to about 5.0 MBq/µg. In another embodiment, the average specific activity of the drug product is from about 2.0 to about 4.0 MBq/µg. In another embodiment, the average specific activity of the drug product is from about 2.5 to about 3.5 MBq/µg. In yet another embodiment, the average specific activity of the drug product is about 0.5 MBq/µg, about 1.0 MBq/µg, about 1.5 MBq/µg, about 2.0 MBq/µg, about 2.5 MBq/µg, about 3.0 MBq/µg, about 3.5 MBq/µg, about 4.0 MBq/µg, about 4.5 MBq/µg, about 5.0 MBq/µg, about 6.0 MBq/µg, about 7.0 MBq/µg, about 8.0 MBq/µg, about 9.0 MBq/µg, or about 10.0 MBq/µg at time of calibration.

In yet another embodiment, the fill volume of the drug product in the vial is from about 1 mL to about 10 mL, from about 2 mL to about 8 mL, from about 3 mL to about 6 mL, or from about 3.6 mL to about 4.4 mL. In yet another embodiment, the fill volume of the drug product in the vial is about 1 mL, about 2 mL, about 3 mL, about 3.6 mL, about 4 mL, about 4.4 mL, about 5 mL, about 6 mL, about 7 mL, about 8 mL, about 9 mL or about 10 mL.

In another embodiment, the pH of the drug product is from about 4.5 to about 8.0, from about 4.6 to about 7.9, from about 4.7 to about 7.8, from about 4.8 to about 7.7, from about 4.9 to about 7.6, from about 5.0 to about 7.5, or from about 5.5 to about 7.5. In another embodiment, the pH of the drug product is 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0 7.1, 7.2, 7.3, 7.4, or 7.5.

In one embodiment, the content uniformity of the drug product is ≤10%, ≤9%, ≤8%, ≤7%, ≤6%, ≤5%, ≤4%, 3%, ≤2%, ≤1%, ≤0.9%, ≤0.8%, ≤0.7%, ≤0.6%, ≤0.5%, ≤0.4%, ≤0.3%, ≤0.2%, or ≤0.1%.

In another embodiment, ethanol is present in the drug product in an amount from about 1% to about 10%, from about 2% to about 9%, from about 3% to about 8%, from about 4% to about 7%, or from about 4% to about 6%. In yet another embodiment, ethanol is present in the drug product in an amount about 1%, about 2%, about 3%, about 4%, about 5%, about 6%, about 7%, about 8%, about 9%, about 10%.

In one embodiment, the ascorbic acid content in the drug product is from about 1 mg/mL to about 100 mg/mL, from about 10 mg/mL to about 90 mg/mL, from about 20 mg/mL to about 80 mg/mL, from about 3 mg/mL to about 70 mg/mL, from about 40 mg/mL to about 60 mg/mL, from about 30 mg/mL to about 60 mg/mL, or from about 36 mg/mL to about 44 mg/mL. In another embodiment, the ascorbic acid content in the drug product is about 1 mg/mL, about 10 mg/mL, about 15 mg/mL, about 20 mg/mL, about 30 mg/mL, about 36 mg/mL, about 40 mg/mL, about 44 mg/mL, about 50 mg/mL, about 60 mg/mL, about 70 mg/mL, about 80 mg/mL, about 90 mg/mL or about 100 mg/mL.

In one embodiment, the RCP of the drug product is ≥90%, ≥91%, ≥92%, ≥93%, ≥94%, ≥95%, ≥96%, ≥97%, ≥98%, or ≥99%.

In another embodiment, the drug product has an isolated radiochemical yield (RCY) of about 50%, about 55%, about 56%, about 60%, about 65%, about 68%, about 70%, about 75%, about 80%, about 83%, about 85%, about 90% or about 95% (decay corrected).

In one embodiment, the Filter Integrity Test is conducted on the drug product. In another embodiment, the sterility of the drug product is tested.

iv. Dosage of the Drug Product

As for the drug product dose employed herein, the present disclosure provides for an effective amount of $^{64}$Cu- DOTATATE sufficient to allow positron emission tomography (PET) imaging in a subject in need thereof.

In one embodiment, the dose of the drug product administered to a subject in need thereof is from about 20 MBq to about 350MBq, from about 30 MBq to about 340 MBq, from about 40 MBq to about 330 MBq, from about 50 MBq to about 320 MBq, from about 60 MBq to about 310 MBq, from about 70 MBq to about 300 MBq, from about 80 MBq to about 290 MBq, from about 90 MBq to about 280 MBq, from about 100 MBq to about 270 MBq, from about 110 MBq to about 260 MBq, from about 132 MBq to about 163 MBq or from about 111 MBq to about 185 MBq or from about 120 MBq to about 250 MBq at calibration date and time.

In another embodiment, the dose of the drug product administered to a subject in need thereof is about 20 MBq, about 30 MBq, about 37 MBq, about 40 MBq, about 50 MBq, about 60 MBq, about 70 MBq, about 80 MBq, about 90 MBq, about 100 MBq, about 110 MBq, about 111 MBq, about 120 MBq, about 130 MBq, about 140 MBq, about 148 MBq, about 150 MBq, about 160 MBq, about 170 MBq, about 180 MBq, about 185 MBq, about 190 MBq, about 200 MBq, about 210 MBq, about 220 MBq, about 230 MBq, about 240 MBq, about 250 MBq, about 260 MBq, about 270 MBq, about 280 MBq, about 290 MBq, about 300 MBq, about 310 MBq, about 320 MBq, about 330 MBq, about 340 MBq, or about 350 MBq at calibration date and time.

In one embodiment, the dose of the drug product administered to a subject in need thereof is from about 0.5 mCi to about 9.5 mCi, from about 0.54 mCi to about 9.0 mCi, from about 0.6 mCi to about 8.5 mCi, from about 0.7 mCi to about 8 mCi, from about 0.8 mCi to about 7.5 mCi, from about 0.9 mCi to about 7 mCi, from about 1.0 mCi to about 6.5 mCi, from about 1.1 mCi to about 6 mCi, from about 1.2 mCi to about 5.5 mCi, from about 1.3 mCi to about 5.0 mCi, from about 1.4 mCi to about 4.5 mCi, from about 1.5 mCi to about 4.0 mCi, from about 2 mCi to about 3 mCi, from about 0.1 mCi to about 10 mCi, from about 0.5 mCi to about 5 mCi, from about 1 mCi to about 5 mCi, or from about 1 mCi to about 4 mCi at calibration date and time.

In yet another embodiment, the dose of the drug product administered to a subject in need thereof is about 0.1 mCi, about 0.5 mCi, about 0.54 mCi, about 0.6 mCi, about 0.7 mCi, about 0.8 mCi, about 0.9 mCi, about 1.0 mCi, about 1.1 mCi, about 1.2 mCi, about 1.3 mCi, about 1.4 mCi, about 1.5 mCi, about 2.0 mCi, about 2.5 mCi, about 3.0 mCi, about 3.1 mCi, about 3.2 mCi, about 3.3 mCi, about 3.4 mCi, about 3.5 mCi, about 3.6 mCi, about 3.7 mCi, about 3.8 mCi, about 3.9 mCi, about 4.0 mCi, about 4.1 mCi, about 4.2 mCi, about 4.3 mCi, about 4.4 mCi, about 4.5 mCi, about 4.6 mCi, about 4.7 mCi, about 4.8 mCi, about 4.9 mCi, about 5.0 mCi, about 5.5 mCi, about 6.0 mCi, about 6.5 mCi, about 7.0 mCi, about 7.5 mCi, about 8.0 mCi, about 8.5 mCi, about 9.0 mCi, about 9.5 mCi, or about 10.0 mCi at calibration date and time.

In one embodiment, the dose of the drug product is administered intravenously. In another embodiment, the drug product is intravenously introduced to a subject in need thereof in a single dose, 2 doses, 3 doses, of multiple doses.

In one particular embodiment, the drug product is administered in a dose of about 148 MBq (or about 4mCi) as an intravenous bolus injection to a subject and images are acquired about 45 to about 90 minutes after drug administration.

Dose selection for an elderly patient should be cautious, usually starting at the low end of the dosing range, reflecting the greater frequency of decreased hepatic, renal, or cardiac function, and of concomitant disease or other drug therapy.

In one embodiment, the drug product is administered to a subject over a period of about 15 minutes, about 10 minutes, about 5 minutes, about 4 minutes, about 3 minutes, about 2 minutes, or about 1 minute.

In one particular embodiment, the amount of radioactivity to be administered for PET imaging in adults is 148 MBq (4mCi) administered as an intravenous injection over a period of approximately one minute.

In one specific embodiment, the drug product comprises 148 MBq (4 mCi) at a concentration of 37 MBq (1 mCi) per 1 mL of $^{64}$Cu-DOTATATE in a single-dose vial at time of calibration.

v. Imaging

Somatostatin analogs competitively bind to the same somatostatin receptors as $^{64}$Cu-DOTATATE and may affect imaging. Patients are imaged just prior to dosing with somatostatin analogs. For patients on long-acting somatostatin analogs, a wash-out period of 28 days is recommended prior to imaging. For patients on short-acting somatostatin analogs, a washout period of 2 days is recommended prior to imaging.

For the drug product PET imaging, a whole-body acquisition from the skull vertex to mid-thigh is recommended. Image acquisition begins between about 45 to about 90 minutes after the intravenous administration of the drug product. The drug product uptake time and scan duration are adapted according to the equipment used and the patient and tumor characteristics, to obtain the optimal image quality.

G. Method of Administration of the Drug Product $^{64}$Cu-DOTATATE binds to somatostatin receptors. Based upon the intensity of the signals, PET images obtained using $^{64}$Cu-DOTATATE Injection indicate the presence and density of somatostatin receptors in tissues. Uptake can also be seen in a variety of non-NET tumors that contain somatostatin receptors or as a normal physiologic variant. NET tumors that do not bear somatostatin receptors will not be visualized.

The method of administration of the drug product to a patient comprises the steps of:
(a) calibrating a $^{64}$Cu-DOTATATE injection,
(b) using the $^{64}$Cu-DOTATATE injection within about 2 hours after calibration time,
(c) using aseptic technique and radiation shielding when withdrawing and administering $^{64}$Cu-DOTATATE injection,
(d) inspecting the $^{64}$Cu-DOTATATE injection visually for particulate matter and discoloration before administration and only using it if the solution does not contain particulate matter or is discolored.
(e) calculating the necessary volume to administer based on measured activity, volume, calibration time, and date,
(f) using a dose calibrator to measure the patient dose immediately prior to administration of the drug product,
(g) after injection of the $^{64}$Cu-DOTATATE injection, an intravenous flush of 0.9% sodium chloride injection, USP is administered to the patient, and
(h) any unused drug is disposed in a safe manner in compliance with applicable regulations.

Estimated radiation absorbed doses per injected activity for organs and tissues of adult patients following an intravenous administration of $^{64}$Cu-DOTATATE injection are shown in Table 4.

TABLE 4

Estimated radiation absorbed dose per injected activity in selected organs with $^{64}$Cu-DOTATATE injection

| Target Organ | Mean* absorbed dose (mGy/MBq) |
|---|---|
| Adrenals | 0.137 |
| Brain | 0.013 |
| Breasts | 0.013 |
| Gallbladder wall | 0.040 |
| Lower large intestine wall | 0.043 |
| Small intestine | 0.066 |
| Stomach wall | 0.019 |
| Upper large intestine wall | 0.022 |
| Heart wall | 0.019 |
| Kidneys | 0.139 |
| Liver | 0.161 |
| Lungs | 0.017 |
| Muscle | 0.019 |
| Ovaries | 0.019 |
| Pancreas | 0.093 |
| Red marrow | 0.027 |
| Osteogenic cells | 0.034 |
| Skin | 0.012 |
| Spleen | 0.115 |
| Testes | 0.014 |
| Thymus | 0.015 |
| Thyroid | 0.014 |
| Urinary bladder wall | 0.037 |
| Uterus | 0.019 |
| Total body | 0.025 |
| Effective dose (mSv/MBq) | 0.032 |

*Mean of 5 patients.

The effective radiation dose resulting from the administration of 148 MBq (4 mCi) to an adult is about 4.7 mSv. For an administered activity of 148 MBq (4 mCi) the typical radiation dose to the critical organs, which are the liver, the kidneys/adrenals, and the spleen, are about 24 mGy, 21 mGy and 17 mGy, respectively. Because the spleen has one of the highest physiological uptakes, higher uptake and radiation dose to other organs or pathologic tissues may occur in patients with splenectomy.

Non-radioactive somatostatin analogs and $^{64}$Cu-DOTATATE competitively bind to somatostatin receptors (SSTR2). Patients are imaged just prior to dosing with somatostatin analogs. For patients on long-acting somatostatin analogs, a wash-out period of 28 days is recommended prior to imaging. For patients on short-acting somatostatin analogs, a washout period of 2 days is recommended prior to imaging.

The uptake of $^{64}$Cu-DOTATATE reflects the level of somatostatin receptor density in NETs, however, uptake can also be seen in a variety of other tumors that also express somatostatin receptors. Increased uptake might also be seen in other non-cancerous pathologic conditions that express somatostatin receptors including thyroid disease or in subacute inflammation, or might occur as a normal physiologic variant (e.g., uncinate process of the pancreas).

A negative scan after the administration of the drug product in patients who do not have a history of NET disease does not rule out disease.

After 1 to 3 hours of a single dose administration of $^{64}$Cu-DOTATATE injection, the maximum radioactivity is observed in adrenal glands, kidney, pituitary glands, spleen, and liver.

Following a single intravenous dose (4.15±0.13 mCi) of $^{64}$Cu-DOTATATE injection (n=6), between 16% to 40% radioactivity of the injected dose was recovered in urine over a 6-hour collection time.

In one embodiment, following a single intravenous dose of $^{64}$Cu-DOTATATE injection, about 5%, about 10%, about 15%, about 16%, about 20%, about 25%, about 30%, about 35%, about 40%, about 45% or about 50% radioactivity of the injected dose is recovered in urine over a 6-hour collection time.

In another embodiment, following a single intravenous dose of $^{64}$Cu-DOTATATE injection, about 5%, about 10%, about 15%, about 16%, about 20%, about 25%, about 30%, about 35%, about 40%, about 45% or about 50% radioactivity of the injected dose is recovered in urine over a 5-hour collection time.

In yet another embodiment, following a single intravenous dose of $^{64}$Cu-DOTATATE injection, about 5%, about 10%, about 15%, about 16%, about 20%, about 25%, about 30%, about 35%, about 40%, about 45% or about 50% radioactivity of the injected dose is recovered in urine over a 4-hour collection time.

In one embodiment, following a single intravenous dose of $^{64}$Cu-DOTATATE injection, about 5%, about 10%, about 15%, about 16%, about 20%, about 25%, about 30%, about 35%, about 40%, about 45% or about 50% radioactivity of the injected dose is recovered in urine over a 3-hour collection time.

In another embodiment, following a single intravenous dose of $^{64}$Cu-DOTATATE injection, about 5%, about 10%, about 15%, about 16%, about 20%, about 25%, about 30%, about 35%, about 40%, about 45% or about 50% radioactivity of the injected dose is recovered in urine over a 2-hour collection time.

In yet another embodiment, following a single intravenous dose of $^{64}$Cu-DOTATATE injection, about 5%, about 10%, about 15%, about 16%, about 20%, about 25%, about 30%, about 35%, about 40%, about 45% or about 50% radioactivity of the injected dose is recovered in urine over a 1-hour collection time.

EXAMPLES

The following examples provide improved processes for making high-purity $^{64}$Cu-labeled DOTATATE. By labeling the DOTATATE with copper at low temperatures (i.e., ≤30° C.), chelation of other metals by DOTATATE can be reduced, thereby providing a higher purity drug product. In addition, these examples provide a useful process for scaling up production of $^{64}$Cu-DOTATATE while maintaining sufficient chemical stability for distributing the drug product to patients. As used in the examples 1-5 described below, the following buffer solutions were prepared.

Sodium acetate/gentisic acid buffer: Gentisic acid (GA) and sodium acetate (NaOAc) were dissolved in high resistivity water (HRW) and the pH of the resulting solution was adjusted using glacial acetic acid or 1 M sodium hydroxide. The solution was further diluted with HRW to achieve the desired concentration of NaOAc and GA.

Sodium ascorbate buffer: Sodium ascorbate was dissolved in HRW. The pH of the solution was adjusted to 6.5-7.5 using 1 M HCl or 1 M NaOH. The solution was further diluted with HRW to achieve the desired concentration of sodium ascorbate.

Sodium ascorbate/ethanol buffer: Sodium ascorbate was dissolved in HRW and absolute ethanol. The pH was adjusted to 6.5-7.5 with either 1 M HCl or 1 M NaOH and then further diluted with HRW to achieve the desired final concentration of both sodium ascorbate and ethanol.

HPLC was performed using an Agilent 1200 series system equipped with a variable wavelength UV-Vis detector followed in-line with a sodium iodide detector (Bioscan B-FC-200P). A Phenomenex Luna C18 column (150 mm×4.6 mm, 5 µm) was used. The mobile phase was made of Solvent A and Solvent B. Solvent A was a 0.1% trifluoroacetic acid (TFA) in HRW, and solvent B was 0.1% TFA acid in acetonitrile (ACN). The gradient was (i) 15-40% Solvent B in A for 10 min, 40% Solvent B in A from 10 to 15 min, 15% Solvent B in A from 15-16 min, and 15% Solvent B in Solvent A from 16-19 min. The flow rate was 1.2 mL/min, and UV detection was monitored at 220 nm.

Example 1: Preparation of Non-Radioactive Cu-DOTATATE

Figure 2:
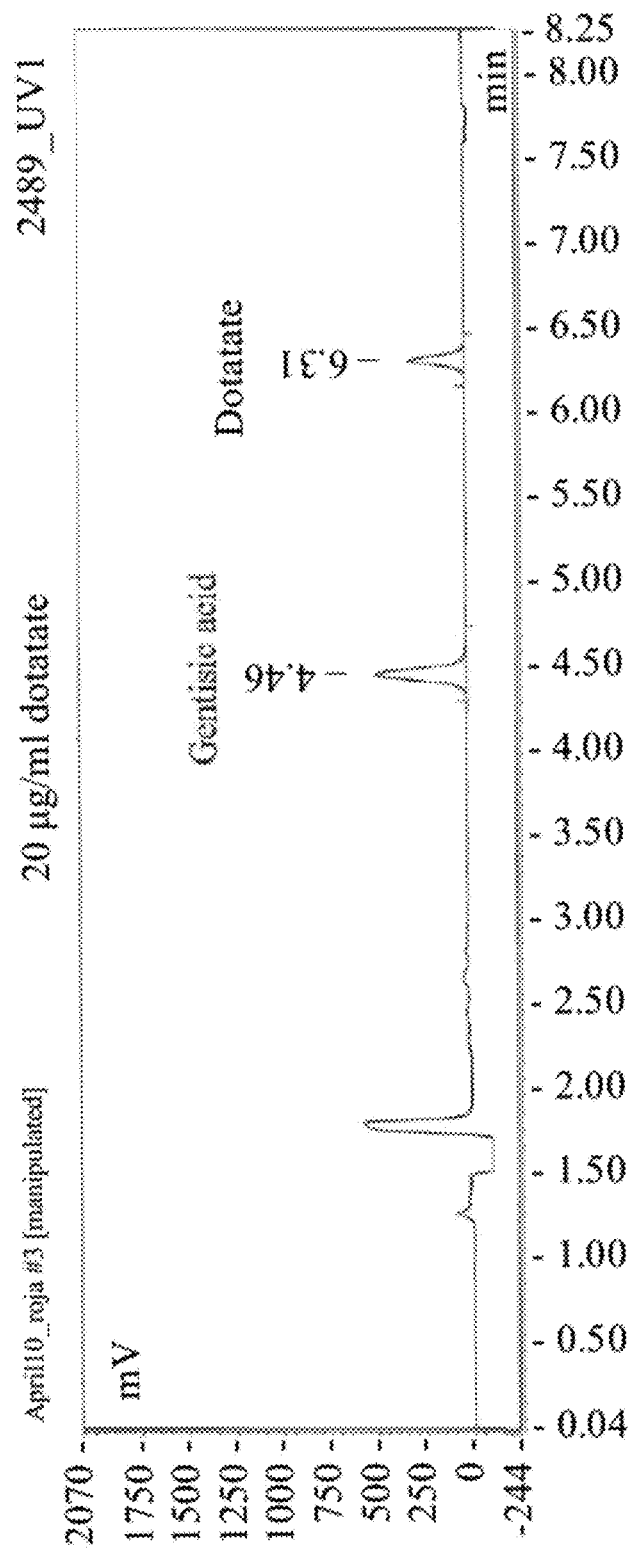
FIG. 2 presents a representative HPLC chromatogram of a standard solution of gentisic acid and DOTATATE.

Initial non-radioactive reactions were performed to prepare Cu-DOTATATE by mixing a solution of $CuCl_2$ in 0.05 M HCl with a solution of DOTATATE peptide in a gentisic acid/sodium acetate buffer solution. The pH of the buffer solution was 6 unless otherwise noted. Formation of Cu-DOTATATE was confirmed via HPLC. The relative retention times of the DOTATATE starting material, Cu-DOTATATE product peaks and other reaction components were established. A representative chromatogram is shown for a standard solution containing gentisic acid/and DOTATATE in FIG. 2.

Figure 3:
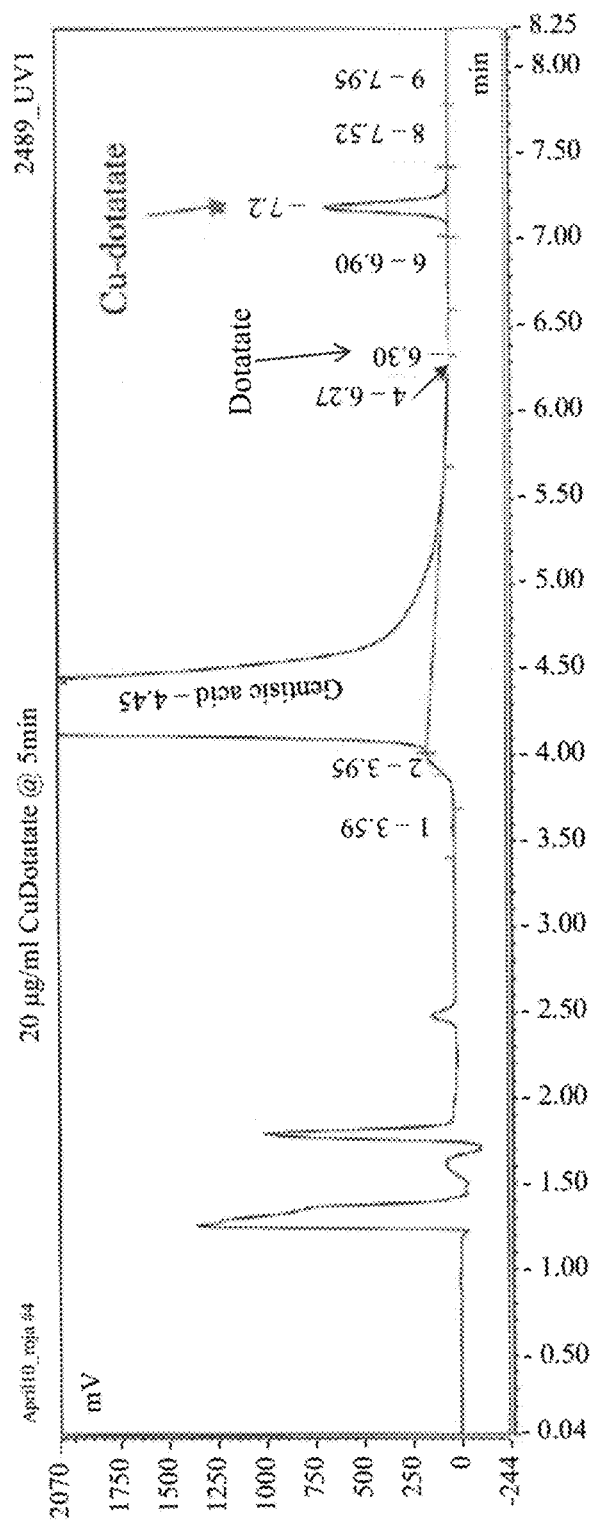
FIG. 3 presets a representative HPLC chromatogram of a crude Cu-DOTATATE reaction mixture after equimolar amounts of DOTATATE and Cu were mixed for 5 minutes at room temperature.

In an initial experiment, approximately equimolar amounts of DOTATATE (0.035 µmol) in NaOAc/GA buffer and copper metal cation (0.039 µmol) in 0.05 M HCl were mixed in a vial at room temperature. The reaction mixture was analyzed by HPLC at multiple time intervals. The HPLC chromatogram for the sample collected at 5 min presented in FIG. 3 showed a new product peak identified as Cu-DOTATATE at approximately 7.2 min that corresponded to a reduction in the DOTATE precursor peak (retention time approximately 6 min). The data suggest that formation of Cu-DOTATATE is rapid and quantitative at ambient temperature and in reaction mixtures containing equimolar amounts of starting material.

Example 2—Formation of Metal DOTATATE Complexes Favors Copper Over Other Common Metals Due to the high specific activity of Cu-64, in a typical [$^{64}$Cu]$Cu^{2+}$ solution, there will be nano- to microgram quantities of $Cu^{2+}$ present. Other trace metals that may be present in the [$^{64}$Cu]$Cu^{2+}$ solution are typically environmental impurities introduced by the manufacturing process. Common transition metals that might be present include iron, lead, zinc and nickel. The effect that metallic impurities may have on the preparation of Copper Cu 64 Dotatate was assessed using non-radioactive solutions of $^{nat}$Cu as a surrogate for $^{64}$Cu in these experiments because they are chemically identical.

A 0.05 M HCl solution containing 0.44 µg (0.00692 µmol) of Cu was mixed with 100 µg (0.0693 µmol) of DOTATATE in a sodium acetate/gentisic acid buffer at room temperature (~22° C.) to provide a molar ratio of DOTATATE to Cu of 10:1. The reaction was monitored by HPLC. As shown in Table 5, the HPLC peak areas for the DOTATATE and Cu-DOTATE compounds exhibit essentially no change in peak area results from the 5 min and 7 h time points, which indicates that the formation of Cu-DOTATATE was rapid and complete after 5 minutes at room temperature.

TABLE 5

Peak areas for DOTATATE and Cu-DOTATATE as a function of reaction time.

| Reaction Time (Approximate) | DOTATATE Peak Area (mV/min) | Cu-DOTATATE Peak Area (mV/min) | DOTATATE: Cu-DOTATE Peak Ratio |
|---|---|---|---|
| 5 min | 43.19 | 4.62 | 9.3 |
| 7 h | 43.06 | 4.72 | 9.1 |

Since isotopically enriched $^{64}$Ni is typically used in the production of $^{64}$Cu, Ni is another potential metallic impurity. However, since it is difficult to achieve HPLC baseline resolution between Ni-DOTATATE and Cu-DOATATE a similar competition experiment was performed using Ni as a surrogate for Cu to evaluate the reaction kinetics of Ni. A non-radioactive labeling reaction was performed by mixing a solution of Ni (0.0063 µmol), Fe (0.0069 µmol), Zn (0.0067 µmol), and Co (0.0068 µmol) in 0.05 M HCl with a solution of DOTATATE (0.0693 µmol) in gentisic acid/sodium acetate buffer at room temperature (~22° C.). No copper was added to the solution to better evaluate the chelation behavior of Ni in the presence of Fe, Zn, and Co.

The reaction mixture was analyzed by HPLC at both 5 min and 6 h timepoints. The peak area results are summarized in Table 6 and demonstrate that the reaction kinetics of $Ni^{2+}$ with DOTATATE are much slower than for $Cu^{2+}$. Therefore, similar to other transition metals (e.g, Fe, Co, Zn) it appears that Cu chelation by DOTATATE also occurs faster than Ni at ambient temperatures.

TABLE 6

HPLC Analysis Results for Experiment 9 (Peak Areas for DOTATATE and metal-DOTATATE compounds)

| Approx. Reaction Time | Peak Area- DOTATATE (mV/min) | Peak Area- Ni- DOTATATE (mV/min) | Peak Area- Fe/Co/Zn- DOTATATE (mV/min) | DOTATATE: Total Metals Peak Ratio (mV/min) |
|---|---|---|---|---|
| 5 min | 34.64 | 0.09 | 7.95 | 4.3:1 |
| 6 h | 28.33 | 5.01 | 15.55 | 1.4:1 |

Example 3—Formation of Cu-DOTATATE at Lower Temperatures

A similar experiment to those described in Example 2 was performed to determine whether Cu-DOTATATE formation occurred similarly at reduced temperatures (i.e., 15° C. to 18° C.). Reaction mixtures were prepared as described in Example 2 but were adjusted as needed to meet the conditions outlined in Table 7.

TABLE 7

Labeling conditions tested at lower temperatures

| Reaction | DOTATATE (µmol) | Cu (µmol) | Fe (µmol) | DOTATATE: Cu molar ratio | DOTATATE: Fe molar ratio |
|---|---|---|---|---|---|
| 1 | 0.0693 | 0.00692 | 0 | 10:1 | N/A |
| 2 | 0.0693 | 0.0175 | 0 | 4:1 | N/A |
| 3 | 0.0693 | 0.0175 | 0.0183 | 4:1 | 4:1 |

Each reaction mixture was sampled for HPLC analysis after approximately 5 min. The reaction mixtures containing only Cu were also sampled after almost 2 h. The results are summarized in Table 8. These data confirm that labeling DOTATATE is largely complete after 5 minutes, even at reduced temperatures and in the presence of Fe.

TABLE 8

HPLC analysis of Cu-DOTATATE reactions performed at lower temperatures

| Reaction | DOTATATE Peak Area (mV/min) | Cu-DOTATATE Peak Area (mV/min) | Fe-DOTATATE Peak Area (mV/min) | DOTATATE:Cu-DOTATATE Peak Ratio | DOTATATE:Fe-DOTATATE Peak Ratio |
|---|---|---|---|---|---|
| 1 (5 min) | 41.36 | 4.49 | N/A | 9.2:1 | N/A |
| 1 (1.7 h) | 41.59 | 4.77 | N/A | 8.7:1 | N/A |
| 2 (5 min) | 35.71 | 11.38 | N/A | 3.14:1 | N/A |
| 2 (1.7 h) | 35.72 | 11.94 | N/A | 3.10:1 | N/A |
| 3 (5 min) | 33.63 | 10.84 | 2.17 | 3.1:1 | 15.5:1 |

Example 4—Preparation of Up to 2,000 mCi of $^{64}$Cu-DOTATATE in a Single Reaction Radiolabeling reactions followed the general procedure described herein. A solution of $^{64}$Cu in 0.05 M HCl was mixed with a solution of DOTATATE in sodium acetate/gentisic acid buffer. The reaction mixture was heated to 30° C. for 5 min and then purified via a C-18 solid phase extraction cartridge. The purified $^{64}$Cu-DOTATATE was collected in 2 mL of 50% EtOH and subsequently diluted with an ascorbic acid solution. The final product was assayed for activity and the radiochemical purity (RCP) was evaluated via radio-HPLC analysis. Characterization was performed against non-radioactive DOTATATE ($t_R$=6.3 min) and Cu-DOTATATE ($t_R$=7.3 min) standards.

In general, scale up reactions from 100 mCi to approximately 7,000 mCi of Cu-64 were achieved for a single reaction. Representative reactions for 100 mCi-7000 mCi batch sizes and results are outlined in Table 9. HPLC analyses showed the primary product peak had a retention time ($t_R$) of approximately 7.4 min, which co-eluted with non-radioactive Cu-DOTATATE ($t_R$=7.3 min). The remainder of the activity eluted ($t_R$=6.2-7.2 min) are attributed to degradation products due to radiolysis. The chemical stability of the purified reaction solutions was monitored by HPLC and demonstrated that $^{64}$Cu-DOTATATE was stable over a period of at least 47 h, as shown in Table 9.

TABLE 9

Summary of representative $^{64}$Cu-DOTATATE reactions from approximately 100 to 2000 mCi

| $^{64}$Cu Activity at TOS (mCi) | Total DOTATATE (μg) | Reaction Volume (mL) | Purified $^{64}$Cu-DOTATATE (mCi) | Isolated RCY[a] | RCP[b] | Day 1 (+24 hr) | Day 2 (+47 hr) |
|---|---|---|---|---|---|---|---|
| 120.6 | 200 | 1.5 | 88.3 | 73.2% | 98.9% | 97.7% | 95.0% |
| 481 | 1000 | 1.5 | 374 | 77.8% | 99.4%[c] | 99.7%[c] | 99.4%[c] |
| 1190 | 2000 | 3.0 | 1070 | 89.5% | 99.6%[c] | 99.4%[c] | 99.7%[c] |
| 2402 | 4000 | 6.0 | 1991 | 82.9% | 99.2%[c] | 99.4%[c] | 99.3%[c] |
| 7297 | 4378 | 13.2 | 6866 | 94.1% | 95% | NP | 95% |

NP = not performed

[a]Decay-corrected to TOS

[b]RCP of the Sep-Pak purified material

[c]Average of two samples

Example 5—Preparation of More than 7,500 mCi of $^{64}$Cu-DOTATATE

Higher batch sizes of $^{64}$Cu-DOTATATE can be prepared by combining two sub-batches. For example, two radiolabeling reactions comprised of 5,250 mCi $^{64}$Cu (R1) and 4,800 mCi $^{64}$Cu (R2) were performed to prepare approximately 9 Ci total of copper Cu 64 dotatate (not decay corrected to time of synthesis). Two separate 5 Ci $^{64}$Cu radiolabeling reactions were performed by mixing $^{64}$Cu in 0.05 M HCl with a solution of DOTATATE in gentisic acid/sodium ascorbate buffer at a ratio of 0.6 µg DOTATATE per mCi of $^{64}$Cu at time of synthesis. The purified drug product solutions from each radiolabeling reaction were combined and diluted to afford approximately 9 Ci total of $^{64}$Cu-DOTATATE at time of purification. The process yield was ≥95%. The RCP of the final drug product solution at time of release was ≥96%.

Example 6—Maximum 64Cu-DOTATATE Batch Prepared at a Reduced DOTATATE Concentration In prior preparations of $^{64}$Cu-DOTATATE, the DOTATATE ligand was added to the reaction mixture at a ratio of 1 µg DOTATATE per 1 mCi of $^{64}$Cu (i.e., a molar ratio of approximately 170:1 at time of synthesis). To improve the molar activity of the final $^{64}$Cu-DOTATATE, a process improvement was initiated to reduce the amount of DOTATATE in the radiolabeling reaction. Two radiolabeling reactions, reaction 1 (R1) and reaction 2 (R2) were performed at up to 5,250 mCi $^{64}$Cu and up to 4,800 mCi $^{64}$Cu, respectively. For R1, the total DOTATATE labeled was around 3,125 µg or a concentration of ≥276 µg/mL. For R2, the total DOTATATE labeled was around 3,018 µg or a concentration of ≥265 µg/mL. The molar ratio of ligand (i.e., moles of DOTATATE) to radionuclide (i.e., moles of $^{64}$Cu) in the reaction mixture was about 102:1 (R1) and about 99:1 (R2). The mass of ligand (µg) to radioactivity of $^{64}$Cu (mCi) concentration was about 0.6 µg/mCi for each reaction. Each $^{64}$Cu solution in 0.05 M HCl was combined with a solution of DOTATATE in sodium acetate/gentisic acid buffer. The radioactive concentration (RAC) at radiosynthesis of R1 and R2 were ≥460 mCi/mL and ≥421 mCi/mL, respectively. The reactions were held at 30° C. for 5 min and held for 5 min at ambient temperature prior to purification.

The crude reaction mixtures for R1 and R2 were each purified using a C-18 solid phase extraction (SPE) cartridge and the eluates containing the purified product were combined to prepare a bulk solution containing about 8.7 Ci of $^{64}$Cu-DOTATATE (not decay corrected to time of synthesis). The process yield was ≥95% and the radiochemical purity (RCP) of the final drug product solution after dilution was ≥96%.

In another experiment approximately 7 Ci of $^{64}$Cu-DOTATATE were prepared in a single reaction using a DOTATATE ratio of 0.6 µg per mCi of Cu-64 (see Table 9).

Example 7—Effects of Gentisic Acid and Ethanol on $^{64}$Cu-DOTATATE Product Stability The effect of ethanol (EtOH) and gentisic acid (GA) content in the final dose matrix on chemical stability of $^{64}$Cu-dotatate was assessed. In these experiments, 500 mCi reactions were performed using the general procedure outlined in Example 2 and the $^{64}$Cu-DOTATATE product was eluted from the Sep-Pak with 2 mL of 50% EtOH (aq) into 5 mL of 50 mg/mL NaOAsc buffer to serve as the purified $^{64}$Cu-DOTATATE stock solution. From the $^{64}$Cu-DOTATATE stock, 1 mL aliquots were transferred to vials containing the following solutions:

| Vial | Solution |
| --- | --- |
| 1 | 2 mL of 66.3 mg/mL NaOAsc |
| 2 | 2 mL of 132.3 mg/mL NaOAsc |
| 3 | 2 mL of 66.3 mg/mL NaOAsc + 8% EtOH |
| 4 | 2 mL of 66.3 mg/mL NaOAsc + 15 mg/mL GA |
| 5 | 2 mL of 66.3 mg/mL NaOAsc + 30 mg/mL GA |
| 6 | 4 mL of 132.3 mg/mL NaOAsc |
| 7 | 5 mL of 64.8 mg/mL NaOAsc + 2.8% EtOH |
| 8 | 2 mL of 49.5 mg/mL NaOAsc |
| 9 | 2 mL of 94.5 mg/mL NaOAsc |
| 10 | 8 mL of 46.1 mg/mL NaOAsc + 3.5% EtOH |
| 11 | 8 mL of 79.9 mg/mL NaOAsc + 3.5% EtOH |
| 12 | 5 mL of 64.8 mg/mL NaOAsc + 2.8% EtOH |

Each of the vials was analyzed by HPLC for stability, and the results are summarized in Table 10. Surprisingly, the highest amount of degradation (24%-38%) were those that contained high amounts of GA, which is generally considered to be a radioprotectant. In those samples, the decrease in $^{64}$Cu-DOTATATE correlated with an increase in free $^{64}$Cu and two unknown radioimpurities at $t_R$=6.6 min and 7.1 min. It is unlikely that degradation resulted from radiolysis as vials with similar activity concentrations exhibited little to no degradation, and so the mechanism that resulted in chemical instability remains unknown. The only other condition that resulted in more than 2% loss of $^{64}$Cu-DOTATATE over 48 hours was Vial 3, which differed from the control (Vial 1) in that it contained approximately 10% EtOH.

TABLE 10

Percentage of intact $^{64}$Cu-DOTATATE over time under various conditions.

| Vial | Total Volume (mL) | Activity Conc. (mCi/mL) | NaOAsc (mg/mL) | EtOH (%) | GA (mg/mL) | % Complex Day 0[a] | % Complex Day 1[b] | % Complex Day 2[c] |
| --- | --- | --- | --- | --- | --- | --- | --- | --- |
| 1 | 3 | 16.3 | 55 | 4.6 | 0 | 96.4 | 96.2 | 97.4 |
| 2 | 3 | 17.9 | 98 | 4.6 | 0 | 95.5 | 94.3 | 93.9 |
| 3 | 3 | 18.1 | 55 | 9.7 | 0 | 95.2 | 87.2 | 91.0 |
| 4 | 3 | 16.5 | 55 | 4.6 | 10 | 97.0 | 69.6 | 70.2 |
| 5 | 3 | 17.0 | 55 | 4.6 | 20 | 96.6 | 78.7 | 78.2 |
| 6 | 4.5 | 4.1 | 122 | 1.6 | 0 | 96.2 | 96.7 | 97.2 |
| 7 | 6 | 5.4 | 60 | 4.9 | 0 | 97.8 | 97.1 | 97.2 |
| 8 | 3 | 10.6 | 45 | 5.2 | 0 | 98.1 | 96.4 | 97.7 |
| 9 | 3 | 10.6 | 74 | 5.2 | 0 | 97.7 | 97.2 | 99.4 |

TABLE 10-continued

Percentage of intact $^{64}$Cu-DOTATATE over time under various conditions.

| Vial | Total Volume (mL) | Activity Conc. (mCi/mL) | NaOAsc (mg/mL) | EtOH (%) | GA (mg/mL) | % Complex Day 0[a] | % Complex Day 1[b] | % Complex Day 2[c] |
|---|---|---|---|---|---|---|---|---|
| 10 | 9 | 3.6 | 45 | 4.8 | 0 | 97.5 | 96.3 | 100.0 |
| 11 | 9 | 3.6 | 75 | 4.8 | 0 | 96.8 | 97.2 | 97.0 |
| 12 | 6 | 5.4 | 60 | 4.9 | 0 | 97.5 | 97.2 | 98.2 |

[a]Tested at 1-2 h from TOS;
[b]Tested at 24-26 h from TOS;
[c]Tested at 45-48 h from TOS.

The results indicated that $^{64}$Cu-DOTATATE remains chemically stable for two days at greater than 95% purity in solutions containing sodium ascorbate at concentrations ranging from 45-122 mg/mL, ethanol concentrations from 1.6%-5.2% and activity concentrations of 3.6-16 mCi/mL (at time of preparation). The $^{64}$Cu-dotatate product remained stable at greater than 90% purity for solutions containing sodium ascorbate at concentrations of up to 98 mg/mL and ethanol content of up to 9.7% for solutions with activity concentrations of approximately 18 mCi/mL (at time of preparation).

Example 8: Preparation of Cu-DOTATATE in the Presence of Increased Gentisic Acid or Sodium Ascorbate The general reaction scheme used in previous experiments was repeated except that the concentration of gentisic acid in the reaction mixture was increased 4-fold. After the reaction, the mixture was sampled and purified via a C-18 solid phase extraction (SPE) cartridge and the purified product was analyzed via HPLC to determine the reaction yield. Results for the HPLC analyses are summarized in Table 11. Almost quantitative recovery of the DOTATATE and Cu-DOTATATE was achieved and neither labeling efficiency nor purification were affected by a large excess of gentisic acid in the reaction mixture.

TABLE 11

Summary of HPLC Analysis of Cu-DOTATATE Preparation

| Sample | DOTATATE Peak Area (mV/min) | Cu-DOTATATE Peak Area (mV/min) | DOTATATE Yield (%) | Cu-DOTATATE Yield (%) |
|---|---|---|---|---|
| Crude reaction mixture | 151.608 | 7.692 | N/A | N/A |
| Purified product | 145.072 | 7.766 | 95.6% | 101% |

Gentisic acid in the reaction mixture serves as a radioprotectant, and aids in the reduction of radiolytic degradation. To assess the possibility of using another radioprotectant, a reaction was performed wherein sodium ascorbate was added to the reaction mixture (pH=6.8). DOTATATE (0.0693 μmol) in sodium acetate/gentisic acid buffer was mixed with a solution of Cu$^{2+}$ in 0.05 M HCl (0.0069 μmol) and diluted with sodium ascorbate so that the ratio of DOTATATE to Cu$^{2+}$ was 10:1. The reaction mixture was mixed at room temperature and samples were taken at 5 min and 51 min to monitor the formation of the Cu-DOTATATE via HPLC analysis. The HPLC peak area for Cu-DOTATATE was 2.33 mV/min at 5 min and 2.36 mV/min at 51 min indicating that the reaction was complete by 5 min.

Example 9—Effect of Non-Radioactive Copper on Radiochemical Purity of $^{64}$Cu-DOTATATE Three reactions, each using approximately 5 Ci were performed. R1 was a control reaction with no added non-radioactive copper. No copper was detected in R1. Non-radioactive copper was added to R2 and R3 to investigate its impact on RCP. R2 had a total copper content of about 139 μg in 12.6 mL (11.0 μg/mL). R3 had a total copper content of about 476 μg in 15.3 mL (31.1 μg/mL). The total DOTATATE labeled in each reaction was about 3000 μg (R1), about 3000 μg (R2), and about 3600 μg (R3) or a concentration of ≥250 μg/mL, ≥238 μg/mL, and ≥235 μg/mL, respectively. The reaction time for each reaction was about 5 minutes. After heating, each reaction was cooled at room temperature for about 5 minutes and the mixture was subsequently purified and diluted to its final bulk solution.

The R1, R2, and R3 final drug product solutions had a RAC of about 11.7 mCi/mL (R1), about 10.3 mCi/mL (R2), and about 12.4 mCi/mL (R3) respectively. The R1, R2, and R3 decay-corrected process yields were about 95.4%, about 98.7%, and about 95.6%, respectively. The RCP of each final drug product solution after dilution was ≥95.5% (R1), ≥97.3% (R2), and ≥97.9% (R3).

Example 10—Recovery of DOTATATE from an SPE Cartridge at Higher Flow Rates

Typically flow rates through an SPE cartridge are performed at low flow rates (i.e., 1-5 mL/min) to ensure adequate loading of the desired product on the cartridge and high recovery of the purified product eluate. In the case of $^{64}$Cu-DOTATATE, concentrating the product on a SPE cartridge may result in higher radiolytic damage, especially for high activity batches. Therefore, to reduce the purification time the recovery of DOTATATE was evaluated for higher flow rates. Because the C-18 SPE chemistry is driven primarily by DOTATATE interaction with the cartridge the experiment was performed using a non-radioactive solution of DOTATATE, since the behavior of Cu-DOTATATE or other metal-DOTATATE species is very similar.

Figure 4:
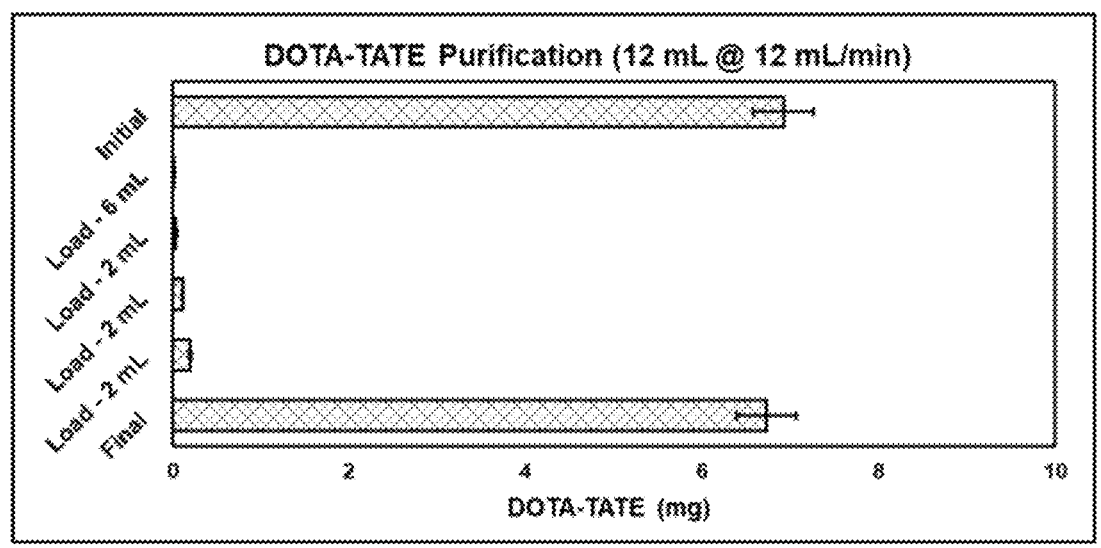
FIG. 4 presents the recovery of DOTATATE in the fractionated load solution (12 mL total) and the final 50% EtOH eluate at a 12 mL/min flow rate.
Figure 5:
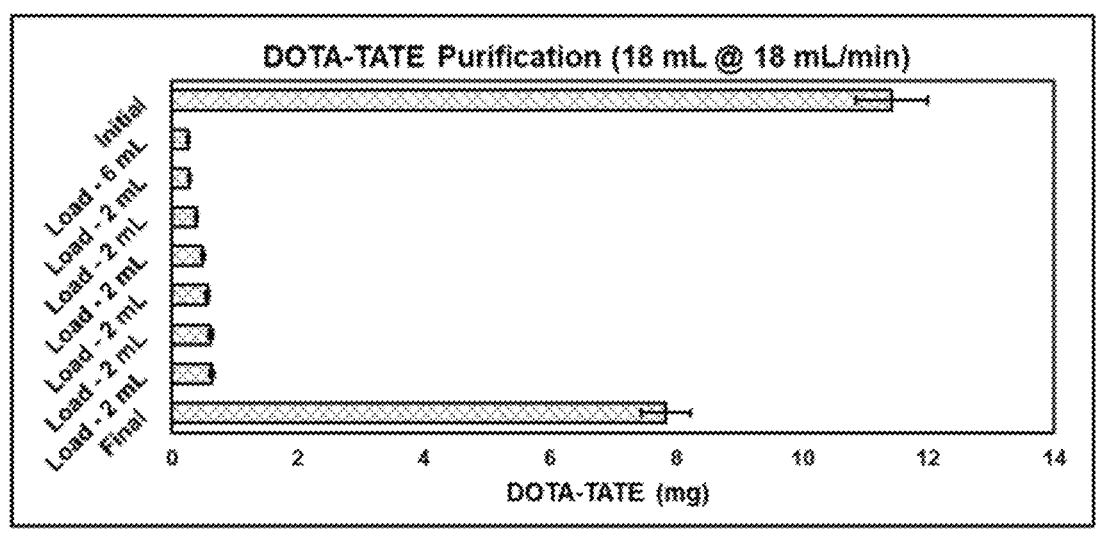
FIG. 5 presents the recovery of DOTATATE in the fractionated load solution (18 mL total) and the final 50% EtOH eluate at an 18 mL/min flow rate.

A solution of DOTATATE in sodium acetate/gentisic acid buffer was prepared and loaded onto a C-18 SPE cartridge at either a flow rate of 12 mL/min or 18 mL/min. The cartridge was rinsed with water and the DOTATATE was eluted in 50% EtOH. The quantity of DOTATATE in the load solution and the purified product eluate were assessed via HPLC. At a flow rate of 12 mL/min, 5.3% of the DOTATATE broke through the SPE cartridge during the load while 97.1% was recovered in the eluate (total recovery 102%). When purification was performed at 18 mL/min 28.4% of the DOTATATE broke through during loading and 68.7% was recovered in the eluate (total recovery 97%). The results indicate that flow rates of at least up to 12 mL/min can be utilized for the purification of $^{64}$Cu-DOTATATE while maintaining near quantitative recovery yields. The load solution was collected in fractions and the DOTATATE recovery results for the individual fractions are presented in FIG. 4 and FIG. 5.

Example 11—Improved Purification Yield of Cu-DOTATATE Using 50% Ethanol Eluent Typically, radiolabeled Copper Cu-64 Dotatate is purified by C-18 SPE. In this procedure, the crude radiolabeling solution was loaded onto a C-18 SPE cartridge, the cartridge rinsed with water to remove hydrophilic impurities, and then the purified copper $^{64}$Cu-DOTATATE compound is typically eluted from the cartridge using 100% ethanol. We have found that the purification yield of Cu-DOTATATE can be improved by using 50% EtOH. Several experiments were conducted to support this observation.

Reaction mixtures containing copper (2+) ions, transition metal ion impurities, and the bioconjugate chelator (DOTATATE) were prepared in triplicate for each condition. The reaction mixtures were held at room temperature (approx. 20° C.) for 5 min and then purified using a C-18 SPE cartridge and were eluted either in 100% EtOH (n=3) or with 50% EtOH (n=3). The DOTATATE to metal ratios in the reaction mixture are provided in Table 12.

TABLE 12

Molar Ratio DOTA-TATE to Metal Ions for Labeling

| Metal Ion | DOTA-TATE: Metal Molar Ratio |
|---|---|
| Cu (2+) | 4:1 |
| Fe (3+) | 4:1 |
| Co (3+) | 8:1 |
| Pb (2+) | 8:1 |
| Total Metals | 1.3:1 |

Approximately 10 min after mixing a sample of the crude reaction mixture was analyzed by HPLC to obtain the in situ reaction yield. Afterwards, each reaction mixture was purified by via a C-18 SPE cartridge and the product was eluted with either 100% EtOH or 50% EtOH. The isolated yield of the purified product solutions was determined by HPLC analysis. The results are provided in Table 13. Reaction yields were determined by comparison to DOTATATE standards.

TABLE 13

Comparison of Isolated Yields for Cu-DOTATATE Using 50% EtOH or 100% EtOH Eluates

| Compound | % EtOH in Eluent | Avg In Situ Yield[1] | Avg Isolated Yield[1,3] |
|---|---|---|---|
| Cu-DOTA-TATE | 50% | 91% | 83% |
|  | 100% | 88% | 48% |
| Fe/Co-DOTA-TATE[4] | 50% | 32% | 28% |
|  | 100% | 32% | 20% |

TABLE 13-continued

Comparison of Isolated Yields for Cu-DOTATATE Using 50% EtOH or 100% EtOH Eluates

| Compound | % EtOH in Eluent | Avg In Situ Yield[1] | Avg Isolated Yield[1,3] |
|---|---|---|---|
| Pb-DOTA-TATE | 50% | 83% | 74% |
|  | 100% | 80% | 37% |

[1]Average from n = 3 preparations.
[2]Fe/Co-DOTATATE peaks were not baseline resolved and were integrated as a single peak

Example 12—Efficacy of the Drug Product

The efficacy of the drug product was established in two single-center, open-label studies. Study 1 prospectively evaluated a total of 63 subjects, including 42 patients with known or suspected NET based on histology, conventional imaging, or clinical evaluations and 21 healthy volunteers. Of the 42 patients, 37 (88%) had a history of NETs at the time of the drug product imaging. Among the total study population of 63 subjects, 28 (44%) were men and 35 (56%) were women with most subjects being white (86%). The mean age of the subjects was 54 years (range 25 to 82 years).

The drug product images from each subject were interpreted as either positive or negative for NET by three independent readers who were blinded to clinical information and other imaging results. PET imaging results were compared to a composite reference standard consisting of a single oncologist's blinded assessment of subject diagnosis based on available histopathology results, reports of conventional imaging (MRI, contrast CT, bone scintigraphy, [$^{18}$F]fluorodeoxyglucose PET/CT, [$^{18}$F]sodium fluoride PET/CT, [$^{111}$In]indium pentetreotide SPECT/CT, [$^{68}$Ga]Ga-dotatate PET/CT) performed within 8 weeks prior to the drug product imaging, and clinical and laboratory data including chromogranin A and serotonin levels. The proportion of subjects positive for disease per composite reference who were identified as positive by drug product imaging was used to quantify positive percent agreement. The proportion of subjects without disease per composite reference who were identified as negative by drug product imaging was used to quantify negative percent agreement. Table 14 shows the performance of the drug product in the detection of NET for Study 1.

TABLE 14

Performance of the drug product in the detection of NET by reader in Study 1

| NET status as identified by reader | | Reference | |
|---|---|---|---|
| | | Positive | Negative |
| Reader 1 (n = 62)* | Positive | 30 | 1 |
| | Negative | 3 | 28 |
| | Percent Reader Agreement (95% CI)** | 91 (75, 98) | 97 (80, 99) |
| Reader 2 (n = 63) | Positive | 30 | 6 |
| | Negative | 3 | 24 |
| | Percent Reader Agreement (95% CI)** | 91 (75, 98) | 80 (61, 92) |

TABLE 14-continued

Performance of the drug product
in the detection of NET by reader in Study 1

| NET status as identified by reader | Reference Positive | Negative |
|---|---|---|
| Reader 3 Positive | 30 | 3 |
| (n = 63) Negative | 3 | 27 |
| Percent Reader Agreement (95% CI)** | 91 (75, 98) | 90 (72, 97) | n: number of patients,
CI: confidence interval,
*Reader 1 interpreted one of the 63 PET scans as "not evaluable",
**Wilson score interval with continuity correction Study 2 showed similar performance through retrospective analysis of published data collected in 112 patients (63 males, 49 females; mean age 62 years, range 30 to 84 years) with a known history of NET.

Example 13—Safety and Efficacy of the Drug Product

In safety and efficacy trials, 71 subjects received a single dose of the drug product. Of these 71 subjects, 21 were healthy volunteers and the remainder were patients with known or suspected NET. The following adverse reactions occurred at a rate of ≤2%: (a) Gastrointestinal Disorders: nausea, vomiting; and (b) Vascular Disorders: flushing.

126 patients with known history of NET received a single dose of $^{64}$Cu-DOTATATE injection. Four patients were reported to have experienced nausea immediately after injection.

The embodiments described herein are intended to be merely exemplary. Persons skilled in the art will understand that variations and modifications may be made without departing from the scope of the invention encompassed by the claims below.

The invention claimed is:

1. A drug product for use in positron emission tomography comprising $^{64}$Cu-DOTATATE ($^{64}$Cu—N-[(4,7,10-tricarboxymethyl-1,4,7,10-tetrazacyclododec-1-yl)acetyl]-(D)-phenylalanyl-(L)-cysteinyl-(L)-tyrosyl-(D)-tryptophanyl-(L)-lysyl-(L)-threoninyl-(L)-cysteinyl-(L)-threonine-cylcic disulfide (Cys$^2$-Cys$^7$)), wherein the drug product comprises a molar ratio of total DOTATATE:total $^{64}$Cu of about 125:1 to about 1:1 and is a single-dose vial containing 148 MBq (4 mCi) of $^{64}$Cu-DOTATATE at calibration date and time in a 4 mL solution volume, wherein the radiochemical purity of the drug product is ≥96%.

2. The drug product of claim 1, wherein the radiochemical purity of the drug product is ≥97%.

3. The drug product of claim 1, wherein the radiochemical purity of the drug product is ≥98%.

4. The drug product of claim 1, wherein the radiochemical purity of the drug product is ≥99%.

5. The drug product of claim 1, wherein the drug product is stable for 48 hours after formulation.

6. The drug product of claim 1, wherein the drug product is stable for 24 hours after formulation.

7. The drug product of claim 1, wherein the molar ratio of total DOTATATE:total $^{64}$Cu is about 125:1 to about 75:1.

* * * * *